(12) United States Patent
Tavares

(10) Patent No.: US 10,981,922 B2
(45) Date of Patent: Apr. 20, 2021

(54) SYNTHESIS OF LACTAMS

(71) Applicant: Francis Xavier Tavares, Durham, NC (US)

(72) Inventor: Francis Xavier Tavares, Durham, NC (US)

( * ) Notice: Subject to any disclaimer, the term of this patent is extended or adjusted under 35 U.S.C. 154(b) by 0 days.

(21) Appl. No.: 16/227,456

(22) Filed: Dec. 20, 2018

(65) Prior Publication Data

US 2019/0119293 A1  Apr. 25, 2019

Related U.S. Application Data

(63) Continuation of application No. 14/396,759, filed as application No. PCT/US2013/037878 on Apr. 24, 2013, now Pat. No. 10,202,392.

(60) Provisional application No. 61/638,491, filed on Apr. 26, 2012.

(51) Int. Cl.
  *C07D 487/14*  (2006.01)
  *C07D 205/08*  (2006.01)

(52) U.S. Cl.
  CPC ......... *C07D 487/14* (2013.01); *C07D 205/08* (2013.01)

(58) Field of Classification Search
  CPC .................................................. C07D 487/14
  See application file for complete search history.

(56) References Cited

U.S. PATENT DOCUMENTS

| 6,506,760 | B1 | 1/2003 | Araldi et al. | |
| 10,202,392 | B2 * | 2/2019 | Tavares | ................ C07D 205/08 |
| 2009/0264401 | A1 | 10/2009 | Gill et al. | |
| 2014/0271466 | A1 | 9/2014 | Sharpless et al. | |

FOREIGN PATENT DOCUMENTS

| WO | WO2000059939 | A1 | 10/2000 | |
| WO | WO-03064423 | A1 * | 8/2003 | .......... C07D 471/14 |
| WO | 2004/047725 | A2 | 6/2004 | |
| WO | WO2006020082 | A1 | 2/2006 | |
| WO | 2006/029153 | A2 | 3/2006 | |
| WO | 2006/031606 | A2 | 3/2006 | |
| WO | 2006/031610 | A2 | 3/2006 | |
| WO | 2007/061677 | A2 | 5/2007 | |
| WO | 2008/073251 | A1 | 6/2008 | |
| WO | 2008/109464 | A1 | 9/2008 | |
| WO | 2010020675 | A1 | 2/2010 | |
| WO | WO-2012061156 | A1 * | 5/2012 | .......... C07D 487/14 |
| WO | WO2012061156 | A1 | 5/2012 | |
| WO | 2013/148748 | A1 | 10/2013 | |
| WO | 2013/169574 | A2 | 11/2013 | |
| WO | WO-2015061407 | A1 * | 4/2015 | |

OTHER PUBLICATIONS

Duan et al., "Palbociclib Commercial Manufacturing Process Development. Part 1: Control of Regioselectivity in a Grignard-Mediated SnAr Coupling" OPR&D, DOI: 10.1021/acs.oprd.6b00070.
International Search Report for PCT/US2013/037878, dated Aug. 8, 2013.

* cited by examiner

*Primary Examiner* — John S Kenyon
(74) *Attorney, Agent, or Firm* — Barnes & Thornburg LLP

(57) ABSTRACT

Methods for the synthesis of lactams are presented whereby a carboxylic acid of the formula HOOC—OR—NH-LG, wherein OR is an organic moiety and LG is a leaving group, is reacted with an acid, such as an organic acid, in particular a strong acid, and a dehydrating agent, which may be one in the same such as a strong acid anhydride, such that the amount of acid added allows for the desired transformation to take place without the loss of the leaving group (LG) before the cyclization, and recovering the lactam.

17 Claims, No Drawings

SYNTHESIS OF LACTAMS

CROSS-REFERENCE TO RELATED APPLICATIONS

This application is a continuation of U.S. application Ser. No. 14/396,759, filed Oct. 24, 2014, which claims priority to PCT Application Number PCT/US2013/037878, with an international filing date of Apr. 24, 2013, which claims priority to U.S. Provisional Patent Application No. 61/638,491 filed on Apr. 26, 2012, each of which is herein incorporated by reference in its entirety.

FIELD OF THE INVENTION

The invention relates to processes to synthesize lactam compounds, such as for pharmaceuticals.

BACKGROUND OF THE INVENTION

There exists a number of approaches for the synthesis of lactams. For example, the classical approach for the synthesis of lactams involves cyclization of the amine onto an ester as exemplified in the Roche case in this patent or N-alkylation followed by acylation onto an acylhalide (Raghavan et al. J Org Chem. 2006 Mar. 3; 71(5): 2151), Rhodium catalyzed intramolecular C—H insertion of alpha-diazo-alpha-(phenylsulfonyl)acetamides derived from alpha-amino acids (Yoon et al., J. Org Chem., 2002, 67 (18) 6582), [2+2] cycloaddition reactions for the synthesis of β-lactams (Bari S. S. et al, Top Heterocycl Chem (2010) 22: 49; Kidwai M. et al. Current Medicinal Chemistry 6(3) 1999, 195). Palladium catalyzed lactam formation (Honda T. et al. Org Lett., 2001, 3(4) 631. Most of these approaches are based on an acylation approach wherein the amine needs to be nucleophilic enough for the transformation to take effect.

SUMMARY OF THE INVENTION

The process invention is directed to the synthesis of a lactam ring of the formula (a)

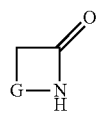

(a)

wherein G represents 1-5 atoms to complete said ring wherein, reading from left to right, G represents: —C— for a 4-membered ring and —C—C—, —C—O—, —O—C—, —N—C, —C—N— for a 5 membered ring and similar arrangements of C, O, N, for 6, 7 and 8-membered rings where any open valences are H or an organic moiety such as alkyl or where open valences represent a ring bonded to adjacent atoms or the same atom as allowed by valence such as a spiro ring, which comprises the steps of
(i) treating a carboxylic acid of the formula (b)

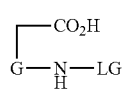

(b)

with an acid such as a strong acid and a dehydrating agent wherein LG is a leaving group such as tBoc such that the amount of strong acid added allows for the desired transformation to take place without the loss of the leaving group (LG) before the cyclization, and
(ii) recovering the lactam (a).

The final product lactams or pharmaceutically acceptable salts thereof may be useful as CDK inhibitors for treatment of diseases and disorders mediated by CDK such as cancer.

DETAILED DESCRIPTION OF THE INVENTION

The invention reactions involving G create cyclic moieties that define 4-8 membered substituted or unsubstituted rings such as β-lactams, pyrrolidones, piperidones to name a few. Lactams of formula (a) may be substituted or unsubstituted 5-8 membered ring systems containing heteroatoms such as oxazolidinones, thiazolidinnes, oxazinanones, thiazinanones, oxazepanones, thiazepanones just to name a few. Besides the use of trifluoroacetic anhydride, other strong acid anhydrides can also be used. For example, tribromoacetic anhydride, trichloroacetic anhydride or mixed anhydrides. In these cases an additional step may be necessary for the removal of LG. In general, most reactions of the invention are conducted at ambient temperature such as about 0-100° C. or about 10-50° C., and involve the use of either nonpolar solvents such as dichloromethane, toluene, benzene, dichloroethane or polar aprotic solvents such as tetrahydrofuran, dioxane or acetonitrile. The dehydrating agent may a carbodiimide-based such as DCC and EDC, an aminium-based agent such as HBTU, TBTU, HATU, HTCU, a phosphonium-based such as BOP, PyBOP, PyAOP, PyBroP, a uronium-based such as TSTU, TOTU, TPTU or another agent such as DEPBT, CDI or T3P. LG may also be an alkylcarbamate, including cyclic and branched chain alkyls, arycarbamates, or heteroarylcarbamates, or alkylamides, arylamides or heteroarylamides (including substituted aryls or heteros). An additional step may be necessary for removal of LG from the cyclized lactam.

As part of the invention, syntheses for intermediates of compounds of formula (I), (II) and (III):

(I)

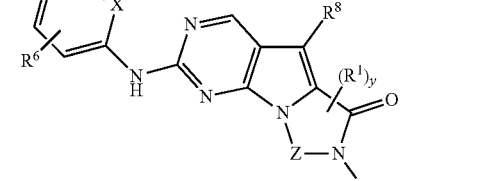

(II)

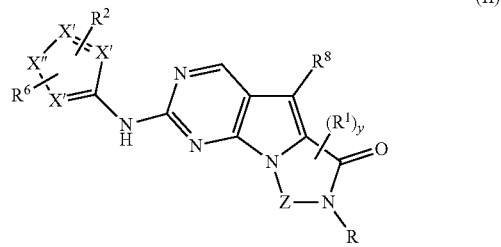

-continued

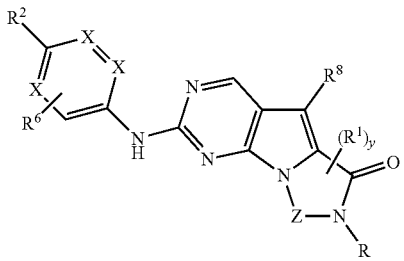

(III)

are provided wherein:

Z is —(CH$_2$)$_x$— wherein x is 1, 2, 3 or 4 or Z is —O—(CH$_2$)$_z$— wherein z is 2, 3 or 4;
each X is independently CH or N;
each X' is independently, CH or N:
X" is CH$_2$, S or NH;
each of R and R$^8$ are independently H, C$_1$-C$_3$ alkyl or haloalkyl;
each R$^1$ is independently aryl, alkyl, cycloalkyl or haloalkyl, wherein each of said alkyl, cycloalkyl and haloalkyl groups optionally includes O or N heteroatoms in place of a carbon in the chain and two R$^1$ groups on adjacent ring atoms or on the same ring atom together with the ring atom(s) to which they are attached optionally form a 3-8-membered cycle;
y is 0, 1, 2, 3 or 4;
R$^2$ is -(alkylene)$_m$-heterocyclo, -(alkylene)$_m$-heteroaryl, -(alkylene)$_m$-NR$^3$R$^4$, (alkylene)$_m$-C(O)—N$^3$R$^4$, -(alkylene)$_m$-C(O)—O-alkyl, -(alkylene)$_m$-OR$^5$, (alkylene)$_m$-S(O)$_n$—R$^5$, or -(alkylene)$_m$-S(O)$_n$—NR$^3$R$^4$ any of which may be optionally independently substituted with one or more R$^x$ groups as allowed by valance, and wherein two R$^x$ groups bound to the same or adjacent atom may optionally combine to form a ring and
wherein m is 0 or 1 and n is 0, 1 or 2;
R$^3$ and R$^4$ at each occurrence are independently:
(i) hydrogen or
(ii) alkyl, cycloalkyl, heterocyclo, aryl, heteroaryl, cycloalkylalkyl, heterocycloalkyl, arylalkyl, or heteroarylalkyl any of which may be optionally independently substituted with one or more R$^x$ groups as allowed by valance, and wherein two R$^x$ groups bound to the same or adjacent atom may optionally combine to form a ring; or R$^3$ and R$^4$ together with the nitrogen atom to which they are attached may combine to form a heterocyclo ring optionally independently substituted with one or more R$^x$ groups as allowed by valance, and wherein two R$^x$ groups bound to the same or adjacent atom may optionally combine to form a ring;
R$^5$ and R$^{5*}$ at each occurrence is:
(i) hydrogen, or
(ii) alkyl, alkenyl, alkynyl, cycloalkyl, heterocyclo, aryl, heteroaryl, cycloalkylalkyl, heterocycloalkyl, arylalkyl, or heteroarylalkyl any of which may be optionally independently substituted with one or more R$^x$ groups as allowed by valance;
R$^x$ at each occurrence is independently, halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylkyl, heterocycloalkyl, -(alkylene)$_m$-OR$^5$, -(alkylene)$_m$-O-alkylene-OR$^5$, -(alkylene)$_m$-S(O)$_n$—R$^5$, -(alkylene)$_m$-NR$^3$R$^4$, -(alkylene)$_m$-CN, -(alkylene)$_m$-(O)—R$^5$, -(alkylene)$_m$-C(S)R$^5$, -(alkylene)$_m$-C(O)—OR$^5$, -(alkylene)$_m$-O—C(O)—R$^5$, -(alkylene)$_m$-(S)—OR$^5$, -(alkylene)$_m$-C(O)-(alkylene)$_m$-NR$^3$R$^4$, -(alkylene)$_m$-C(S)—NR$^3$R$^4$, -(alkylene)$_m$-N(R$^3$)—C(O)—NR$^3$R$^4$, -(alkylene)$_m$-N(R$^3$)—C(S)—NR$^3$R$^4$, -(alkylene)$_m$-N(R$^3$)C(O) R$^5$, -(alkylene)$_m$-N(R$^3$)C(S)R$^5$, -(alkylene)$_m$-OC(O)NR$^3$R$^4$, -(alkylene)$_m$-O—C(S)NR$^3$R$^4$, -(alkylene)$_m$-SO$_2$NR$^3$R$^4$, -(alkylene)$_m$-N(R$^3$)SO$_2$—R$^5$, -(alkylene)$_m$-N(R$^3$)SO$_2$NR$^3$R$^4$, -(alkylene)$_m$-N(R$^3$)C(O)—OR$^5$, -(alkylene)$_m$-N(R$^3$)C(S)—OR$^5$, or (alkylene)$_m$-N(R$^3$)—SO$_2$R$^5$; wherein: said alkyl, haloalkyl, alkenyl, alkynyl, cycloalkyl, cycloalkenyl, heterocyclo, aryl, heteroaryl, arylalkyl, heteroarylalkyl, cycloalkylalkyl, and heterocycloalkyl groups may be further independently substituted with one or more (alkylene)$_m$-CN, (alkylene)$_m$-OR$^{5*}$, -(alkylene)$_m$-S(O)$_n$—R$^{5*}$, (alkylene)$_m$-NR$^{3*}$R$^{4*}$, -(alkylene)$_m$-C(O)—R$^{5*}$, -(alkylene)$_m$-C(=S)R$^{5*}$, (alkylene)$_m$-C(=O)O R$^{5*}$, -(alkylene)$_m$O C(=O)R$^{5*}$, -(alkylene)$_m$-C(S)—OR$^{5*}$, (alkylene)$_m$-C(O)—NR$^{3*}$R$^{4*}$, -(alkylene)$_m$-C(S)—NR$^{3*}$R$^{4*}$, (alkylene)$_m$-N(R$^{3*}$)—C(O)—NR$^{3*}$R$^{4*}$, -(alkylene)$_m$-N(R$^{3*}$)—C(S)—NR$^{3*}$R$^{4*}$, (alkylene)$_m$-N(R$^{3*}$)—C(O)—R$^{5*}$, -(alkylene)$_m$-N(R$^{3*}$)—C(S)—R$^{5*}$, (alkylene)$_m$-O—C(O)—NR$^{3*}$R$^{4*}$, -(alkylene)$_m$-O—C(S)—NR$^{3*}$R$^{4*}$, (alkylene)$_m$-SO$_2$—R$^{3*}$R$^{4*}$, -(alkylene)-N(R$^{3*}$)—SO$_2$—R$^{5*}$, (alkylene)$_m$-N(R$^{3*}$)—SO$_2$—NR$^{3*}$R$^{4*}$, -(alkylene)$_m$N(R$^{3*}$)—C(O)—OR$^{8*}$, (alkylene)$_m$-N(R$^{3*}$)—C(S)—OR$^{5*}$, or -(alkylene)$_m$-N(R$^{3*}$)SO$_2$—R$^{8*}$,
n is 0, 1 or 2, and
m is 0 or 1;
R$^{3*}$ and R$^{4*}$ at each occurrence are independently:
(i) hydrogen, or
(ii) alkyl, alkenyl, alkynyl cycloalkyl, heterocyclo, aryl, heteroaryl, cycloalkylalkyl, heterocycloalkyl, arylalkyl, or heteroarylalkyl any of which may be optionally independently substituted with one or more R$^x$ groups as allowed by valance; or R$^{3*}$ and R$^{4*}$ together with the nitrogen atom to which they are attached may combine to form a heterocyclo ring optionally independently substituted with one or more R$^x$ groups as allowed by valance; and
R$^6$ is H or lower alkyl,
or a pharmaceutically acceptable salt thereof.

In some aspects, the compound is of formula (I) or formula (II) and R$^6$ is hydrogen.

In some aspects, the compound is of formula (III) and the variables are as defined for compounds of formulae (I) and (II) and pharmaceutically acceptable salts thereof.

In some aspects, R$^x$ is not further substituted.

In some aspects, R$^2$ is -(alkylene)$_m$-heterocyclo, -(alkylene)$_m$-heteroaryl, -(alkylene)$_m$NR$^3$R$^4$, -(alkylene)$_m$-C(O)—NR$^3$R$^4$, -(alkylene)$_m$-O—R$^5$, -(alkylene)$_m$-S(O)$_n$—R$^5$, or -(alkylene)$_m$-S(O)$_n$—NR$^3$R$^4$ any of which may be optionally independently substituted with one or more R$^x$ groups as allowed by valance, and wherein two R$^x$ groups bound to the same or adjacent atom may optionally combine to form a ring and wherein m is 0 or 1 and it is 0, 1 or 2.

In some aspects, R$^8$ is hydrogen or C$_1$-C$_3$ alkyl. In some aspects, R is hydrogen or C$_1$-C$_3$ alkyl.

In some aspects, R$^2$ is -(alkylene)$_m$-heterocyclo, -(alkylene)$_m$-NR$^3$R$^4$, -(alkylene)$_m$-C(O)—NR$^3$R$^4$, -(alkylene)$_m$-C(O)—O-alkyl or -(alkylene)$_m$-OR$^5$ any of which may be optionally independently substituted with one or more R$^x$ groups as allowed by valance, and wherein two R$^x$ groups bound to the same or adjacent atoms may combine to form a ring.

In some aspects, R$^2$ is -(alkylene)$_m$-heterocyclo, -(alkylene)$_m$-NR$^3$R$^4$, -(alkylene)$_m$-C(O)—NR$^3$R$^4$, -(alkylene)$_m$C(O)—O-alkyl or -(alkylene)$_m$-OR$^5$ without further substitution.

In some aspects, m in R$^2$ is 1. In a further aspect, the alkylene in R$^2$ is methylene.

In some aspects, $R^2$ is

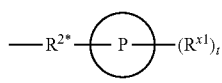

wherein:
$R^{2*}$ is a bond, alkylene$_m$-(alkylene)$_m$-O-(alkylene)$_m$, -(alkylene)$_m$-C(O)-(alkylene)$_m$-, -(alkylene)$_m$-S(O)$_2$-(alkylene)$_m$- or -(alkylene)$_m$-NH-(alkylene)$_m$- wherein each m is independently 0 or 1;
P is a 4- to 8-membered mono- or bicyclic saturated heterocyclyl group;
Each $R^{x1}$ is independently -(alkylene)$_m$-(C(O))$_m$-(alkylene)$_m$-(N(R$^N$))$_m$-(alkyl)$_m$ wherein each m is independently 0 or 1 provided at least one m is 1, —(C(O))—O-alkyl, -(alkylene)$_m$-cycloalkyl wherein m is 0 or 1, —N(R$^N$)-cycloalkyl, —C(O)-cycloalkyl, -(alkylene)$_m$-heterocyclyl wherein m is 0 or 1, or —N(R$^N$)-heterocyclyl, —C(O)-heterocyclyl, —S(O)$_2$-(alkylene)$_m$ wherein m is 1 or 2, wherein:
$R^N$ is H, $C_1$ to $C_4$ alkyl or $C_1$ to $C_6$ heteroalkyl, and wherein two $R^{x1}$ can, together with the atoms to which they attach on P, which may be the same atom, form a ring; and t is 0, 1 or 2.

In some aspects, each $R^{x1}$ is only optionally substituted by unsubstituted alkyl, halogen or hydroxy.

In some aspects, $R^{x1}$ is hydrogen or unsubstituted $C_1$-$C_4$ alkyl.

In some aspects, at least one $R^{x1}$ is -(alkylene)$_m$-heterocyclyl wherein m is 0 or 1.

In some aspects, $R^2$ is of the sub-formula (AA),

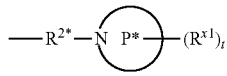

(AA)

wherein P* is a 4- to 8-membered mono- or bicyclic saturated heterocyclyl group.

In some aspects, $R^2$ is

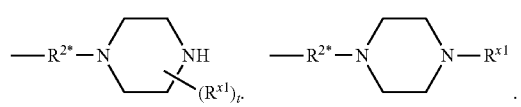

In some aspects, $R^2$ is
In some aspects, $R^2$ is

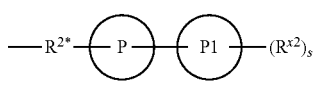

wherein:
$R^{2*}$ is a bond, alkylene, -(alkylene)$_m$-O-(alkylene)$_m$-, -(alkylene)$_m$-C(O) -(alkylene)$_m$-, -(alkylene)$_m$-S(O)$_2$ (alkylene)$_m$- or -(alkylene)$_m$-NH-(alkylene)$_m$- wherein each m is independently 0 or 1; P is a 4- to 8-membered mono- or bicyclic heterocyclyl group;
P1 is a 4- to 6-membered monocyclic saturated heterocyclyl group; each $R^{x2}$ is independently hydrogen or alkyl: and s is 0, 1 or 2.

In some aspects, $R^2$ is

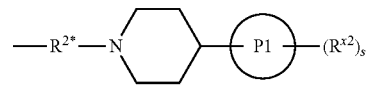

In some aspects, $R^2$ is
In some aspects, P1 includes at least one nitrogen.
In some aspects, any alkylene in $R^{2*}$ in any previous aspect is not further substituted.
In some aspects, $R^2$ is selected from the structures depicted in FIGS. 1-3 of WIPO 2012/061156 published 10 May 2012.
In some aspects, $R^2$ is one of

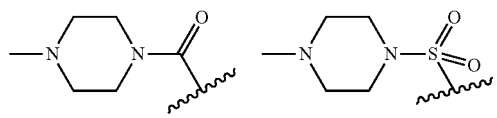

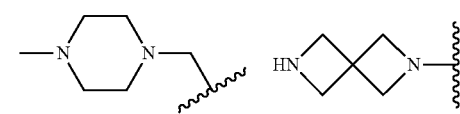

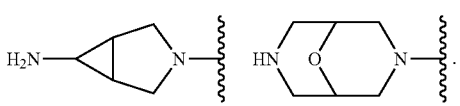

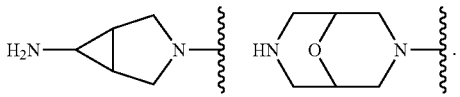

In some aspects, the compound has general formula (I) and more specifically one of the general structures in FIGS. 4-8 of WIPO 2012/061156 published 10 May 2012 wherein the variables are as previously defined.

In some aspects, the compound has general formula (Ia):

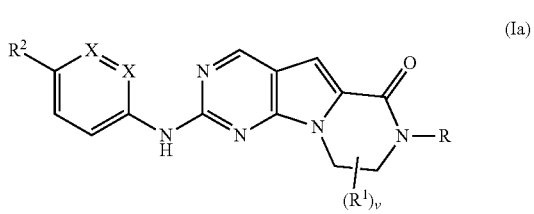

(Ia)

wherein $R^1$, $R^2$, R, X and y are as previously defined.

In some embodiments, the compound has formula (Ia) and R is alkyl or R is H.

In some embodiments, the compound has formula (Ia) and $R^2$ is of the formula (AA) wherein P* is a 4- to 8-membered mono- or bicyclic saturated heterocyclyl group and $R^{2*}$, $R^{x1}$ and t are as previously defined.

In some embodiments, the compound has formula (Ia) and $R^2$ is of the formula (AA) wherein P* is a 4- to 8-membered mono- or bicyclic saturated heterocyclyl group, $R^x$ is hydrogen or unsubstituted $C_1$-$C_4$ alkyl and $R^{2*}$ is as previously defined.

In some embodiments, the compound has formula (Ib):

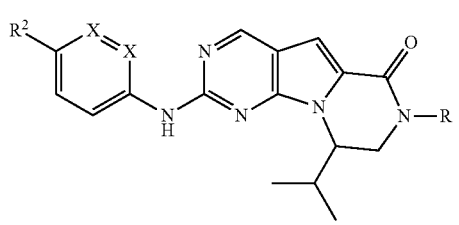

(Ib)

wherein R², X and R are as previously defined.

In some embodiments, the compound has formula (Ib) and R is alkyl or R is H.

In some embodiments, the compound has formula (Ib) and R² is of the formula (AA) wherein P* is a 4- to 8-membered mono- or bicyclic saturated heterocyclyl group and R²*, $R^{x1}$: and t are as previously defined.

In some embodiments, the compound has formula (Ib) and R² is of the formula (AA) wherein P* is a 4- to 8-membered mono- or bicyclic saturated heterocyclyl group, $R^{x1}$ is hydrogen or $C_1$-$C_4$ alkyl and R²* is as previously defined.

In some embodiments, the compound has formula (Ic), (Id), (Ie), (If), (Ig), (Ih), (Ii), (Ij), (Ik), (Il), or (Im):

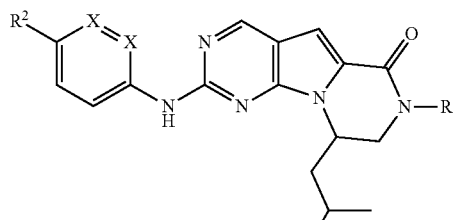

(Ic)

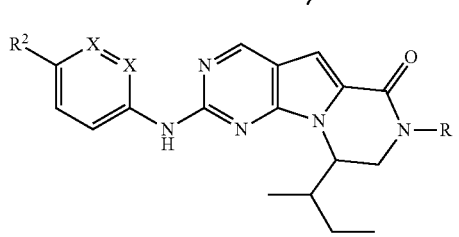

(Id)

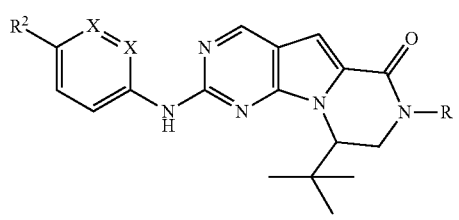

(Ie)

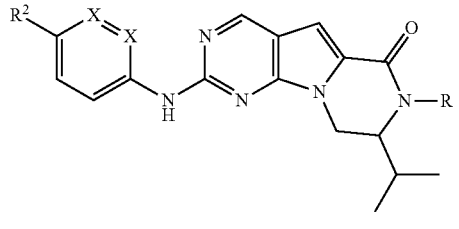

(If)

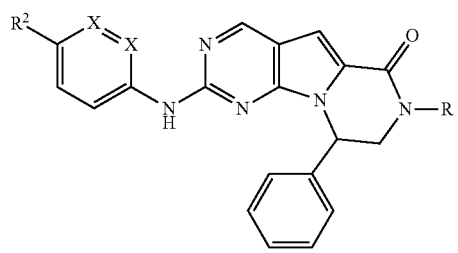

(Ig)

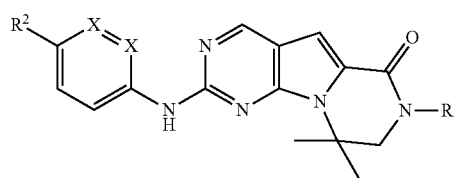

(Ih)

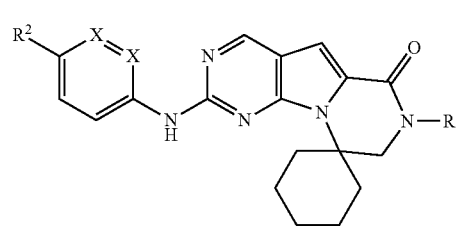

(Ii)

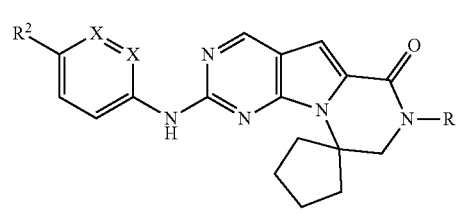

(Ij)

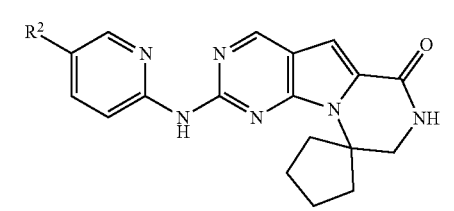

(Ik)

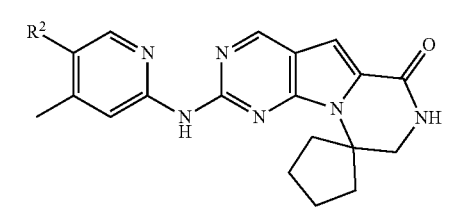

(Il)

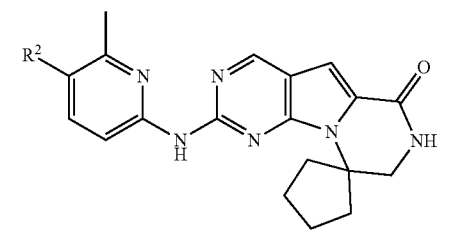

(Im)

In some embodiments, the compound has formula (Ij) and R is H and both X are N.

In some embodiments, the compound has formula (IIa) or (IIb) with R² as defined above:

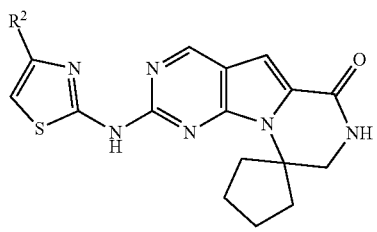

(IIa)

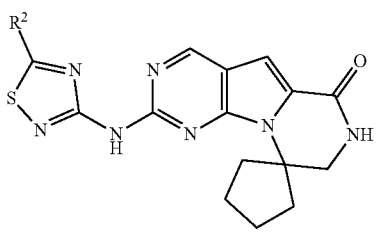

(IIb)

In some embodiments, the compound has formula (IIa) and R² is of the formula (AA) wherein P* is a 4- to 8-membered mono- or bicyclic saturated heterocyclyl group.

In some embodiments, the compound has formula (IIa) and R² is of the formula (AA) wherein P* is a 4- to 8-membered mono- or bicyclic saturated heterocyclyl group and $R^{x1}$ is hydrogen or $C_1$-$C_4$ alkyl.

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg (2007) Advanced Organic Chemistry 5th Ed. Vols. A and B, Springer Science+Business Media LLC, New York. The practice of the present invention will employ, unless otherwise indicated, conventional methods of synthetic organic chemistry, mass spectroscopy, preparative and analytical methods of chromatography, protein chemistry, biochemistry, recombinant DNA techniques and pharmacology. Conventional methods of organic chemistry include those included in March's Advanced Organic Chemistry: Reactions. Mechanisms. and Structure, $6^{th}$ Edition, M. S. Smith and J. March, John Wiley & Sons, Inc., Hoboken, N.J., 2007.

The term "alkyl," either alone or within other terms such as "haloalkyl" and "alkylamino," embraces linear or branched radicals having one to about twelve carbon atoms, "lower alkyl" radicals have one to about six carbon atoms. Examples of such radicals include methyl, ethyl, n-propyl, isopropyl, n-butyl, isobutyl, sec-butyl, tert-butyl, pentyl, isoamyl, hexyl and the like.

The term "alkylene" embraces bridging divalent linear and branched alkyl radicals. Examples include methylene, ethylene, propylene, isopropylene and the like.

The term "alkenyl" embraces linear or branched radicals having at least one carbon-carbon double bond of two to about twelve carbon atoms, "lower alkenyl" radicals having two to about six carbon atoms. Examples of alkenyl radicals include ethenyl, isopropenyl, allyl, propenyl, butenyl and 4-methylbutenyl. The terms "alkenyl" and "lower alkenyl," embrace radicals having "cis" and "trans" orientations, or alternatively, "E" and "Z" orientations.

The term "alkynyl" denotes linear or branched radicals having at least one carbon-carbon triple bond and having two to about twelve carbon atoms, "lower alkynyl" radicals having two to about six carbon atoms. Examples of such radicals include propargyl, butynyl, and the like.

Alkyl, alkenyl, and alkynyl radicals may be optionally substituted with one or more functional groups such as halo, hydroxy, nitro, amino, cyano, haloalkyl, aryl, heteroaryl, heterocyclo and the like.

The term "alkylamino" embraces 'N-alkylamino" and "N,N-dialkylamino" where amino groups are independently substituted with one alkyl radical and with two alkyl radicals, respectively. "Lower alkylamino" radicals have one or two alkyl radicals of one to six carbon atoms attached to a nitrogen atom. Suitable alkylamino radicals may be mono or dialkylamino such as N-mefitylainino, N-ethylamino, N,N-dimethylamino, N,N-diethylamino and the like.

The term "halo" means halogens such as fluorine, chlorine, bromine or iodine atoms. The term "haloalkyl" embraces radicals wherein any one or more of the alkyl carbon atoms is substituted with one or more halo as defined above. Examples include monohaloalkyl, dihaloalkyl and polyhaloalkyl radicals including perhaloalkyl. A monohaloalkyl radical, for one example, may have an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means an alkyl radical having all hydrogen atoms replaced with fluoro atoms. Examples include trifluoromethyl and pentafluoroethyl.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. A particular aryl is phenyl. Said "aryl" group may have 1 or more substituents such as lower alkyl, hydroxyl, halo, haloalkyl, nitro, cyano, alkoxy, lower alkylamino, aryl, heteroaryl, heterocyclo and the like.

The term "heterocyclyl" (or "heterocyclo") embraces saturated, and partially saturated heteroatom-containing ring radicals, where the heteroatoms may be selected from nitrogen, sulfur and oxygen. Heterocyclic rings comprise monocyclic 6-8 membered rings, as well as 5-16 membered bicyclic ring systems (which can include bridged fused and spirofused bicyclic ring systems). It does not include rings containing —O—O—, —O—S— or —S—S portions. Said "heterocyclyl" group may have 1 to 3 substituents such as hydroxyl, Boc, halo, haloalkyl, cyano, lower alkyl, lower aralkyl, oxo, lower alkoxy, amino, lower alkylamino, and the like.

Examples of saturated heterocyclo groups include saturated 3- to 6-membered heteromonocyclic groups containing 1 to 4 nitrogen atoms e.g. pyrrolidinyl. imidazolidinyl, piperidinyl, pyrrolinyl, piperazinyl; saturated 3 to 6-membered heteromonocyclic group containing 1 to 2 oxygen atoms and 1 to 3 nitrogen atoms e.g. morpholinyl, saturated 3 to 6-membered heteromonocyclic group containing 1 to 2 sulfur atoms and 1 to 3 nitrogen atoms e.g., thiazolidinyl.

Examples of partially saturated heterocyclyl radicals include dihydrothienyl, dihydropyranyl, dihydrofuryl, dihydrothiazolyl, and the like.

Particular examples of partially saturated and saturated heterocyclo groups include pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

Heterocycle groups also includes radicals where heterocyclic radicals are fused/condensed with aryl radicals: unsaturated condensed heterocyclic groups containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl e.g., tetrazolo [1,5-b]pyridazinyl, unsaturated condensed heterocyclic group containing 1 to 2 oxygen atoms and 1 to 3 nitrogen atoms e.g. benzoxazolyl, benzoxadiazolyl; unsaturated condensed heterocyclic group containing 1 to 2 sulfur atoms and 1 to 3 nitrogen atoms e.g., benzothiazolyl, benzothiadiazolyl; and saturated, partially unsaturated and unsaturated condensed heterocyclic group containing 1 to 2 oxygen or sulfur atoms e.g. benzofuryl, benzothienyl, 2,3-dihydro-benzo[1,4]dioxinyl and dihydrobenzofuryl.

The term "heteroaryl" denotes aryl ring systems that contain one or more heteroatoms selected from the group O, N and S, wherein the ring nitrogen and sulfur atom(s) are optionally oxidized, and nitrogen atom(s) are optionally quartenized. Examples include unsaturated 5 to 6 membered heteromonocyclyl groups containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl e.g., 4H-1,2,4-triazolyl, 1H-1,2,3-triazolyl, 2H-1,2,3-triazolyl; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl; unsaturated 5 to 6-membered heteromonocyclic groups containing 1 to 2 sulfur atoms and 1 to 3 nitrogen atoms, for example, thiazolyl, thiadiazolyl e.g., 1,2,4-thiadiazolyl, 1,3,4-thiadiazolyl, 1,2,5-thiadiazolyl.

The term "heteroarylalkyl" denotes alkyl radicals substituted with a heteroaryl group. Examples include pyridylmethyl and thienylethyl. The term "sulfonyl", whether used alone or linked to other terms such as alkylsulfonyl, denotes respectively divalent radicals —SO$_2$—. The terms "carboxy" or "carboxyl", whether used alone or with other terms, such as "carboxyalkyl", denotes —C(O)—OH. The term "carbonyl", whether used alone or with other terms, such as "aminocarbonyl", denotes —C(O)—. The term "aminocarbonyl" denotes an amide group of the formula —(C(O)—NH$_2$. The terms "heterocycloalkyl" embrace heterocyclic-substituted alkyl radicals. Examples include piperidylmethyl and morpholinylethyl.

The term "arylalkyl" embraces aryl-substituted alkyl radicals. Examples include benzyl, diphenylmethyl and phenylethyl. The aryl in said aralkyl may be additionally substituted with halo, alkyl, alkoxy, halkoalkyl and haloalkoxy.

The term "cycloalkyl" includes saturated carbocyclie groups of 3 to 10 carbons. Lower cycloalkyl groups include $C_3$-$C_6$ rings. Examples include cyclopentyl, cyclopropyl, and cyclohexyl. Cycloalkyl groups may be optionally substituted with one or more functional groups such as halo, hydroxy, nitro, amino, cyano, haloalkyl, aryl, heteroaryl, heterocyclo and the like.

The term "cycloalkylalkyl" embraces cycloalkyl-substituted alkyl radicals. "Lower cycloalkylalkyl" radicals are cycloalkyl radicals attached to alkyl radicals having one to six carbon atoms. Examples of include eyclohexylmethyl. The cycloalkyl in said radicals may be additionally substituted with halo, alkyl, alkoxy and hydroxy.

The term "cycloalkenyl" includes carbocyclic groups having one or more carbon-carbon double bonds including "cycloalkyldienyl" compounds. Examples include cyclopentenyl, cyclopentadienyl, cyclohexenyl and cycloheptadienyl.

The term "comprising" is meant to be open ended, including the indicated component but not excluding other elements. The term "oxo" as used herein contemplates an oxygen atom attached with a double bond. The term "nitro" as used herein contemplates —NO$_2$. The term "cyano" as used herein contemplates —CN.

Synthesis

The disclosed compounds can be made by the following general schemes:

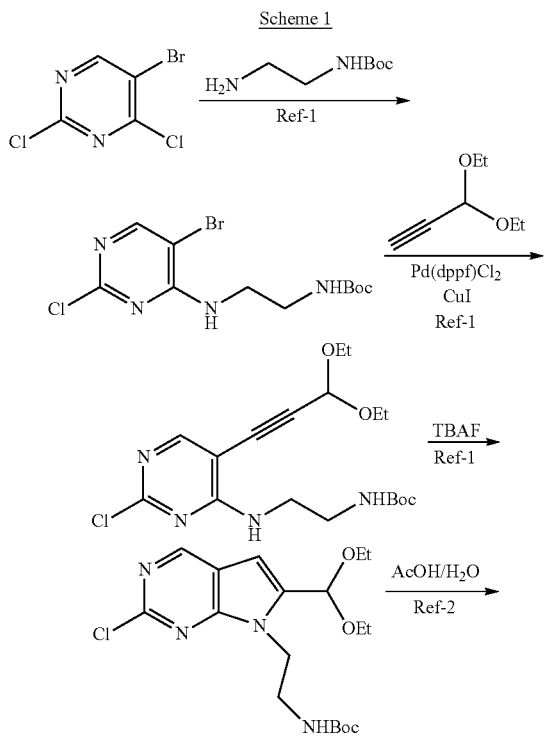

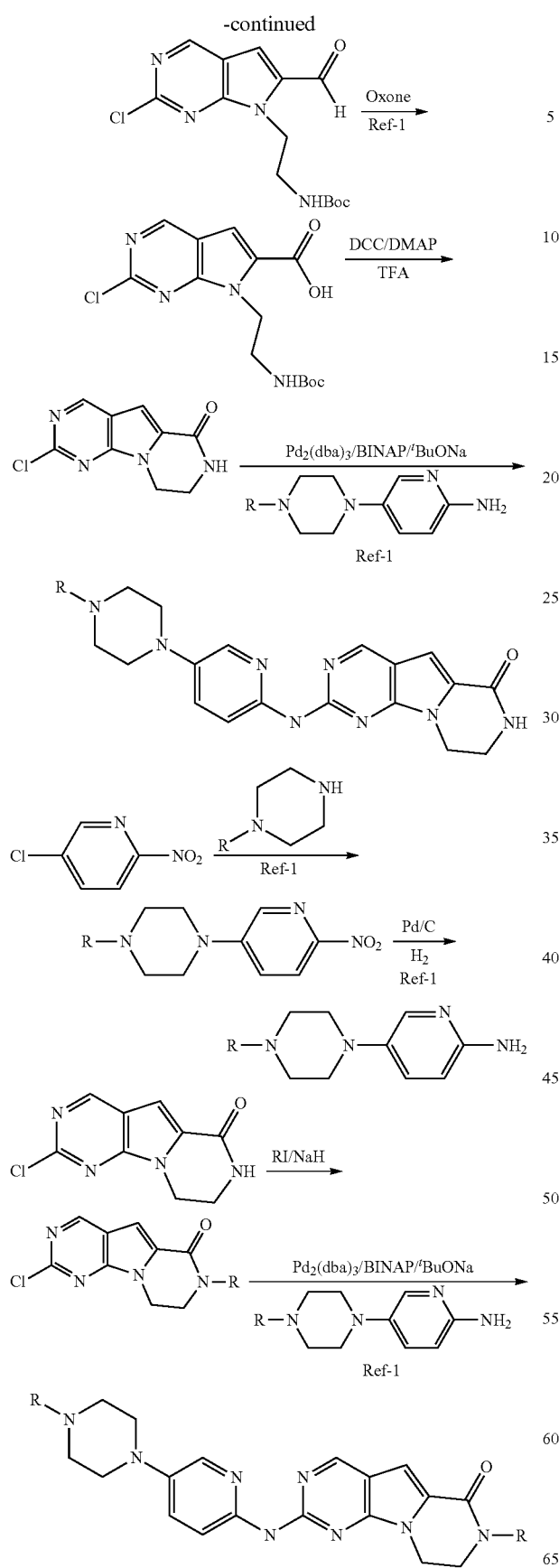
In Scheme 1. Ref-1 is WO 2010/020675 A1; Ref-2 is White, J. D.; et al. *J. Org. Chem.* 1995, 60, 3600; and Ref-3 Presser, A. and Hufner, A. *Monatshefte für Chemie* 2004, 135, 1015.
Scheme 2
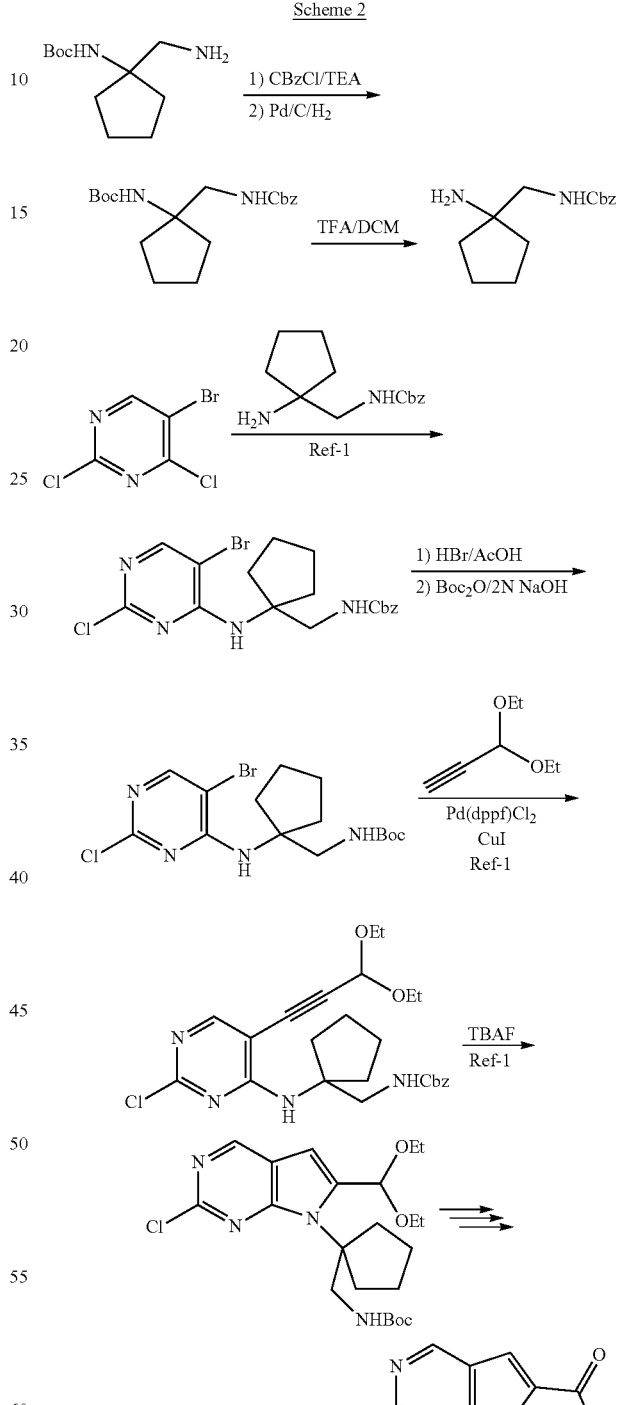
In Scheme 2, Ref-1 is WO 2010/020675 A1.

EXAMPLES

Intermediate 1A

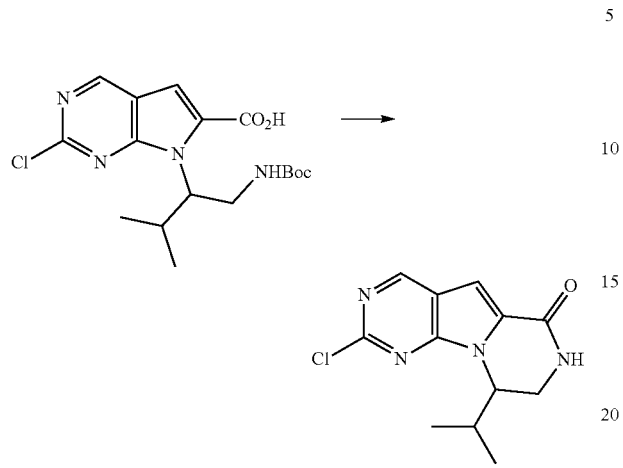

To 7-[1-[(tert-butoxycarbonylamino)methyl]-2-methyl-propyl]-2-chloro-pyrrolo[2,3-d]pyrimidine-6-carboxylic acid 0.050 g (0.00013 mole) in DCM (1.5 ml) was added DIC (32.7 mg) and DMAP (10 mg). The contents were stirred for 2 hrs at room temperature. Trifluoroacetic acid (0.4 ml) was then added and stirring continued for an additional 30 minutes. After addition of satd $NaHCO_3$ to neutralize the excess acid, ethyl acetate was then added and the organic layer separated, dried using magnesium sulfate and then concentrated under vacuum. The crude product was column chromatographed over silica gel using hexane/ethyl acetate (0-100%) to afford Intermediate 1A. 1H NMR (600 MHz, DMSO-$d_6$) δ ppm 0.72 (d, J=6.73 Hz, 3H) 0.97 (d, J=6.73 Hz, 3H) 2.09-2.22 (m, 1H) 3.57 (dd, J=13.18, 4.98 Hz, 1H) 3.72 (dd, J=13.61, 4.25 Hz, 1H) 4.53 (dd, J=8.05, 3.95 Hz, 1H) 7.20 (s, 1H) 8.34 (d, J=4.98 Hz, 1H) 9.08 (s, 1H). LCMS (ESI) 265 (M+H).

Intermediate 1B

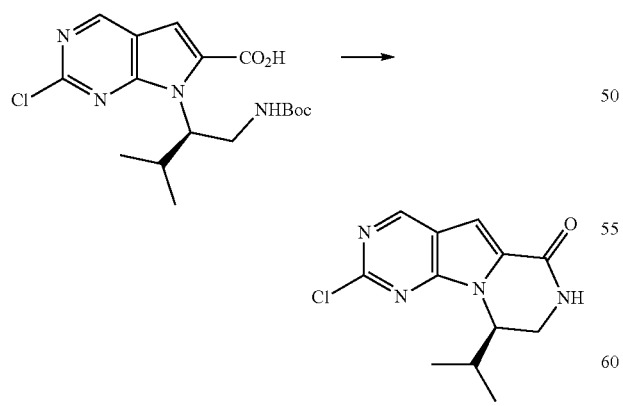

Intermediate 1B was synthesized using analogous reaction conditions as described for Intermediate 1A to afford intermediate 1B. The analytical data is consistent with that reported for the racemate (Intermediate 1A).

Intermediate 1C

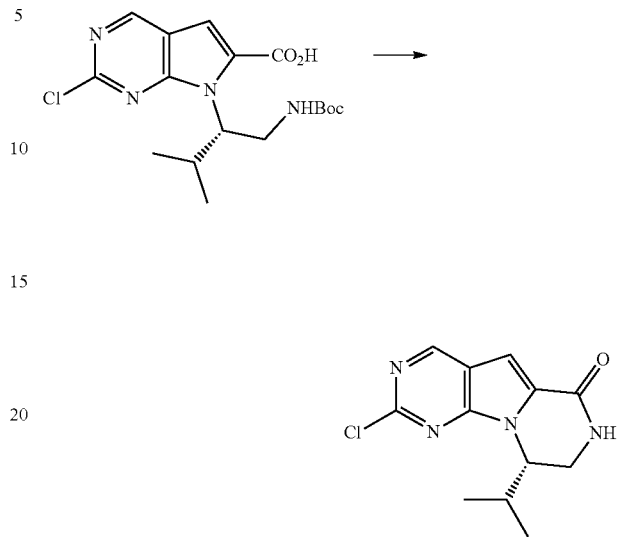

Intermediate 1C was synthesized using analogous reaction conditions as described for Intermediate 1A to afford intermediate 1C. The analytical data is consistent with that reported for the racemate (Intermediate 1A).

Intermediate 1D

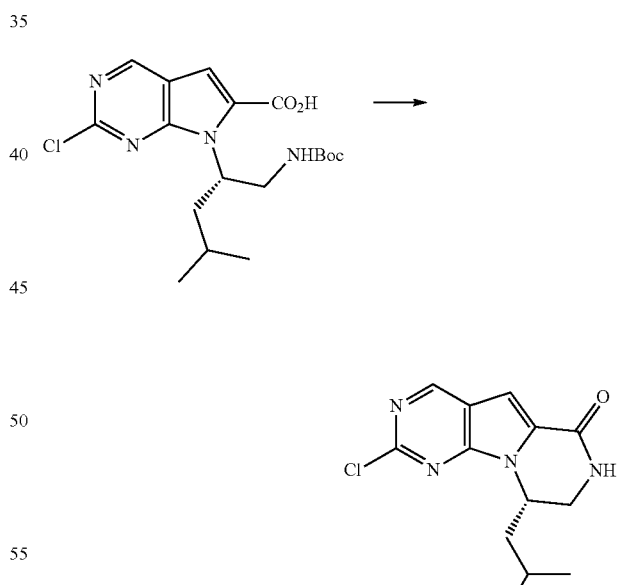

Intermediate 1D was synthesized using analogous reaction conditions as described for Intermediate 1A to afford intermediate 1D. 1H NMR (600 MHz, DMSO-$d_6$) δ ppm 0.82 (d, J=6.73 Hz, 3H) 0.97 (d, J=6.55 Hz, 3H) 1.34-1.46 (m, 1H) 1.48-1.65 (m, 2H) 3.40 (dd, J=13.32, 5.42 Hz, 1H) 3.76 (dd, J=13.47, 4.10 Hz, 1H) 4.76-4.92 (m, 1H) 7.17 (s, 1H) 8.34 (d, J=5.27 Hz, 1H) 9.04 (s, 1H). LCMS (ESI) 279 (M+H).

Intermediate 1E

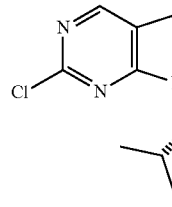 

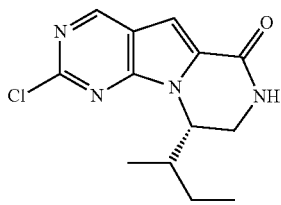

Intermediate 1E was synthesized using analogous reaction conditions as described for Intermediate 1A to afford intermediate 1E. $^1$H NMR (600 MHz. DMSO-d$_6$) δ ppm 0.74 (t, J=7.32 Hz, 3H) 0.89 (d, J=6.73 Hz, 3H) 1.00-1.12 (m, 2H) 1.82-1.94 (m, 1H) 3.55 (dd, J=13.9 1, 4.83 Hz, 1H) 3.70 (dd, J=13.61, 4.25 Hz, 1H) 4.57 (dd, J=7.91, 4.10 Hz, 1H) 7.17 (s, 1H) 8.31 (d, J=5.27 Hz, 1H) 9.05 (s, 1H). LCMS (ESI) 279 (M+H).

Intermediate 1F

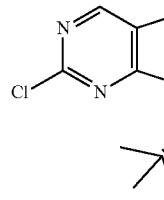 

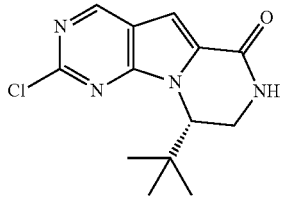

Intermediate 1F was synthesized using an analogous synthetic sequence as that described for intermediate 1A. LCMS (ESI) 279 (M+H).

Intermediate 1G

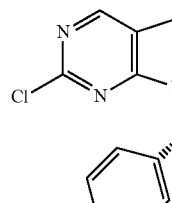 

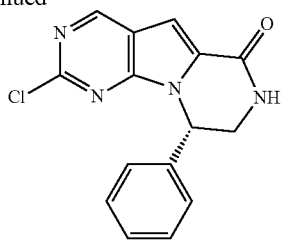

Intermediate 1G was synthesized using an analogous synthetic sequence as that described for intermediate 1A. 1H NMR (600 MHz. DMSO-d$_6$) δ ppm 3.58-3.69 (m, 1H) 4.13 (dd, J=13.47, 4.39 Hz, 1H) 6.07 (d, J=3.81 Hz, 1H) 6.85 (d. J=7.32 Hz, 2H) 7.19-7.31 (m, 3H) 7.34 (s, 1H) 8.27 (d, J=5.27 Hz; 1H) 9.13 (s, 1H). LCMS (ESI) 299 (M+H).

Intermediate 1H

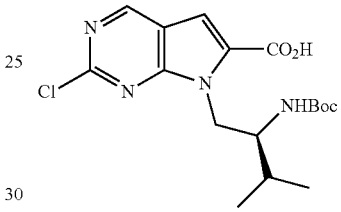 

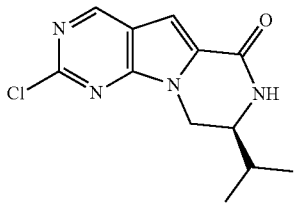

Intermediate 1H was synthesized using an analogous synthetic sequence as that described for intermediate 1A. LCMS (ESI) 265 (M+H).

Intermediate 1I

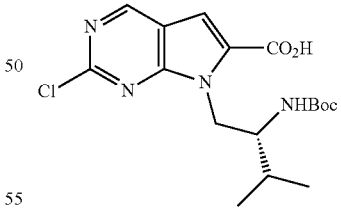 

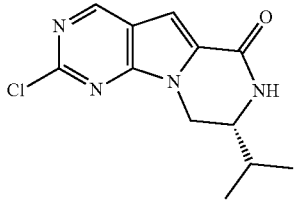

Intermediate 1I was synthesized using an analogous synthetic sequence as that described for intermediate 1A. The analytical data was consistent with that described for its antipode (intermediate 1H). 1H NMR (600 MHz, DMSO-d₆) δ ppm 0.88 (d, J=6.44 Hz, 6H) 1.73-1.86 (m, 1H) 3.67-3.76 (m, 2H) 4.11-4.21 (m, 1H) 7.13-7.19 (m, 1H) 8.56 (s, 1H) 9.05 (s, 1H). LCMS (ESI) 265 (M+H).

Intermediate 1J

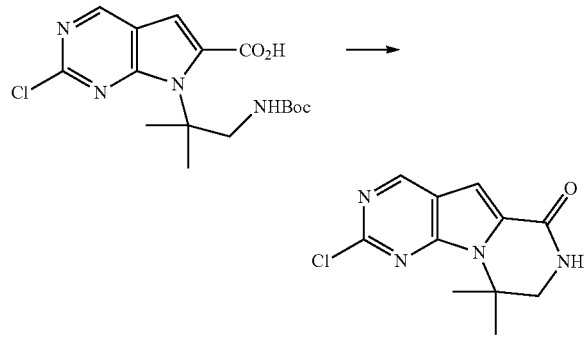

Intermediate 1J was synthesized using an analogous synthetic sequence as that described for intermediate 1A. 1H NMR (600 MHz. DMSO-d₆) δ ppm 1.73 (s, 6H) 3.50 (d. J=2.93 Hz, 2H) 7.25 (s, 1H) 8.46-8.55 (m, 1H) 9.07 (s, 1H). LCMS (ESI) 251 (M+H).

Intermediate 1K

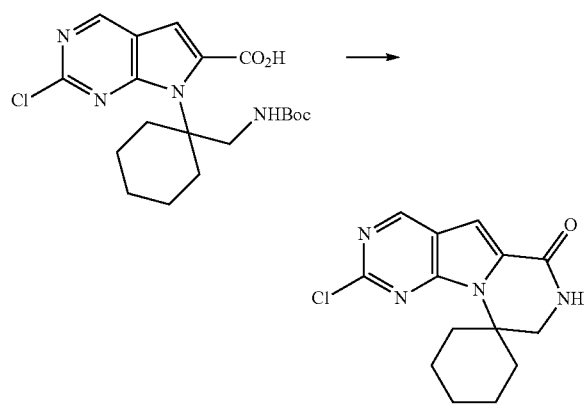

Intermediate 1K was synthesized using an analogous synthetic sequence as that described for intermediate 1A. 1H NMR (600 MHz, DMSO-d₆) δ ppm 1.28 (br. s., 2H) 1.42 (br. s., 2H) 1.70 (br. s., 4H) 1.85-1.95 (m, 2H) 2.69 (m, 2H) 7.16-7.25 (m, 1H) 8.41 (br. s., 1H) 9.04 (s, 1H). LCMS 291 (M+H).

Intermediate 1L

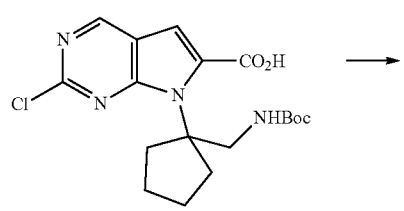

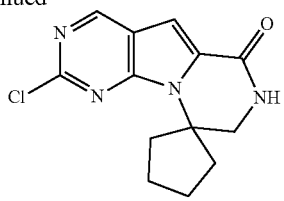

Intermediate 1L was synthesized using an analogous synthetic sequence as that described for intermediate 1A. 1H NMR (600 MHz, DMSO-d₆) ppm 1.72 (br. s., 2H) 1.86-1.93 (m, 2H) 199 (d, J=3.81 Hz, 2H) 2.40 (br. s., 2H) 3.48 (d, J=2.34 Hz, 2H) 7.22 (s, 1H) 8.53 (br. s., 1H) 9.05 (s, 1H). LCMS (ESI) 277 (M+H).

Intermediate 1M

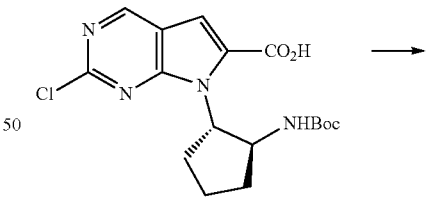

Intermediate 1M was synthesized using an analogous synthetic sequence as that described for intermediate 1A. The analytical data for this racemate is consistent with that described for the L-isomer.

Intermediate 1N

Intermediate 1N was synthesized using an analogous synthetic sequence as that described for intermediate 1A. 1H NMR (600 MHz, DMSO-d₆) δ ppm 1.48-1.60 (m, 1H) 1.88-1.98 (m, 3H) 1.99-2.08 (m, 1H) 2.66-2.75 (m, 1H) 3.63-3.74 (m, 1H) 3.99-4.12 (m, 1H) 7.21 (s, 1H) 8.89 (s, 1H) 9.04 (s, 1H). LCMS (ESI) 263 (M+H).

Also part of the present invention is concerned with the synthesis of tricyclic amide derivatives.

The invention synthesis also relates to intermediates for compounds of the general formula (IV):

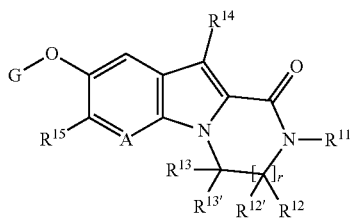

(IV)

wherein for formula (IV)

A is C or N;

R is 1 or 2;

$R^{11}$ is selected from the group consisting of hydrogen, lower alkyl, lower hydroxyalkyl, lower alkoxyalkyl, lower halogenalkyl, lower hydroxyhalogenalkyl, lower alkanoyl, lower alkylsulfonyl, lower phenylsulfonyl, lower cycloalkylalkyl, lower phenylalkyl (wherein the phenyl ring may be unsubstituted or substituted with one or two groups independently selected from lower alkyl, cyano, halogen, lower halogenalkyl, lower alkoxy and lower hydroxyalkyl), lower heteroarylalkyl (wherein the heteroaryl ring may be unsubstituted or substituted with one or two groups independently selected from lower alkyl, halogen, phenyl, lower alkoxy and lower hydroxyalkyl), lower heterocyclylalkyl (wherein the heterocyclyl ring may be unsubstituted or substituted with one or two groups independently selected from lower alkyl, halogen, phenyl, lower alkoxy and lower hydroxyalkyl), and —CH$_2$—CO—NR$^{16}$R$^{17}$, $R^{16}$ and $R^{17}$ independently from each other are selected from the group hydrogen, lower alkyl and phenyl unsubstituted or substituted with one or two groups independently selected from lower alkyl, halogen, lower halogenalkoxy and lower hydroxyalkyl, or $R^{16}$ and $R^{17}$ together with the nitrogen atom to which they are attached form a 4-, 5-, 6- or 7-membered heterocyclic ring optionally containing a further heteroatom selected from nitrogen, oxygen or sulfur, a sulfinyl group or a sulfonyl group, said heterocyclic ring being unsubstituted or substituted by one, two or three groups independently selected from lower alkyl, halogen, halogenalkyl, hydroxyl, lower hydroxyalkyl, lower alkoxy, oxo, phenyl, benzyl, pyridyl and carbamoyl;

$R^{12}$, $R^{12'}$, $R^{13}$ and $R^{13'}$ independently from each other are selected from the group consisting of hydrogen, lower alkyl, lower hydroxyalkyl and lower alkoxyalkyl;

$R^{14}$ is selected from the group consisting of hydrogen and halogen;

$R^{15}$ is hydrogen or halogen;

G is a group selected from G1, G2, G3 and G4

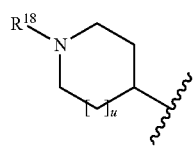

G1

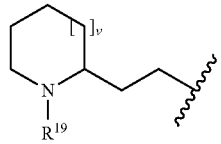

G2

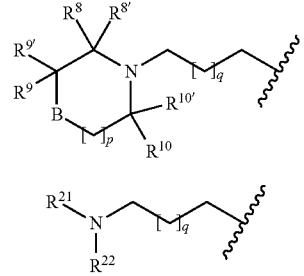

G3

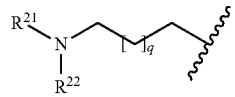

G4 wherein for G1, G2, G3 and G4:

u is 0, 1 or 2;

$R^{18}$ is selected from lower alkyl, cycloalkyl, lower cycloalkylalkyl and lower phenylalkyl;

v is 0, 1 or 2;

$R^{19}$ is lower alkyl;

B is selected from CR$^{23}$R$^{23'}$, O and S;

$R^8$, $R^{8'}$, $R^9$, $R^{9'}$, $R^{10}$, $R^{10'}$, $R^{23}$ and $R^{23'}$ independently from each other are selected from the group consisting of hydrogen, lower alkyl, hydroxyl, halogen and dialkylamino, or $R^9$ and $R^{23}$ together form a double bond;

p is 0, 1 or 2;

q is 0, 1 or 2;

$R^{21}$ is lower alkyl:

$R^{22}$ is lower alkyl;

and pharmaceutically acceptable salts thereof.

The compounds of formula (IV) are antagonists and/or inverse agonists at the histamine 3 receptor (H3 receptor). Their utility is described in WO 2007/065820 published 14 Jun. 2007. The present invention provides a method of creating the lactam ring in (IV) using intermediates in WO 2007/065820 or with minor modifications thereof as known by the art. In particular the intermediate labeled B (R$^2$=H) in scheme 1 of WO 2007/065820 may be used in the present invention by subjecting it to the conditions described for the synthesis of lactams using a strong acid in conjunction with a dehydrating agent or a strong acid anhydride.

An object of the present invention to provide a partial route to the synthesis of selective, directly acting H3 receptor antagonists respectively inverse agonists. Such antagonists/inverse agonists are useful as therapeutically active substances, particularly in the treatment and/or prevention of diseases which are associated with the modulation of H3 receptors.

In the present description for compounds within formula (IV), the term "alkyl," alone or in combination with other groups, refers to a branched or straight-chain monovalent saturated aliphatic hydrocarbon radical of one to twenty carbon atoms, preferably one to sixteen carbon atoms, more preferably one to ten carbon atoms.

Within the formula (IV), the term "lower alkyl" or "C$_1$-C$_8$-alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms. Examples of straight-chain and branched C$_1$-C$_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

Within the formula (IV), the term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl. Especially preferred are cyclopropyl and cyclobutyl. The term "lower cycloalkylalkyl" or "$C_{3-7}$-cycloalkyl-$C_{1-8}$-alkyl" refers to lower alkyl groups as defined above wherein at least one of the hydrogen atoms of the lower alkyl group is replaced by cycloalkyl. A preferred example is cyclopropylmethyl. The term "alkoxy" refers to the group $R^{24}$—O— wherein $R^{24}$ is lower alkyl and the term "lower alkyl" has the previously given significance. Examples of lower alkoxy groups are e.g. methoxy, ethoxy, n-propoxy, isopropoxy, n-butoxy, isobutoxy, sec. butoxy and tert. butoxy, preferably methoxy and ethoxy and most preferred methoxy. The term "lower alkoxyalkyl" or "$C_{1-8}$-alkoxy-$C_{1-8}$-alkyl" refers to lower alkyl groups as defined above wherein at least one of the hydrogen atoms of the lower alkyl groups is replaced by an alkoxy group, preferably methoxy or ethoxy. Among the preferred lower alkoxyalkyl groups are 2-methoxyethyl or 3-methoxypropyl. The term "alkylsulfonyl" or "lower alkylsulfonyl" refers to the group $R^{24}$—S(O)$_2$—, wherein $R^{24}$ is lower alkyl and the term "lower alkyl" has the previously given significance. Examples of alkylsulfonyl groups are e.g. methylsulfonyl or ethylsulfonyl. The term "halogen" refers to fluorine, chlorine, bromine and iodine, with fluorine, chlorine and bromine being preferred. The term "lower halogenalkyl" or "halogen-$C_{1-8}$-alkyl" refers to lower alkyl groups as defined above wherein at least one of the hydrogen atoms of the lower alkyl group is replaced by a halogen atom, preferably fluoro or chloro, most preferably fluoro. Among the preferred halogenated lower alkyd groups are trifluoromethyl, difluoromethyl, trifluoroethyl, fluoromethyl and chloromethyl, with trifluoroethyl being especially preferred. The term "lower hydroxyhalogenalkyl" or "hydroxyhalogen-$C_{1-8}$-alkyl" refers to lower halogenalkyl groups as defined above wherein at least one additional hydrogen atom of the lower alkyl group is replaced by a hydroxy group. A preferred example for a lower hydroxyhalogenalkyl group is 4,4,4-trifluoro-3-hydroxy-butyl. The term "lower halogenalkoxy" or "halogen-$C_{1-8}$-alkoxy" refers to lower alkoxy groups as defined above wherein at least one of the hydrogen atoms of the lower alkoxy group is replaced by a halogen atom, preferably fluoro or chloro, most preferably fluoro. Among the preferred halogenated lower alkyl groups are trifluoromethoxy, difluoromethoxy, fluormethoxy and chloromethoxy, with trifluoromethoxy being especially preferred. The term "lower hydroxyalkyl" or "hydroxy-$C_{1-8}$-alkyl" refers to lower alkyl groups as defined above wherein at least one of the hydrogen atoms of the lower alkyl group is replaced by a hydroxy group. Examples of lower hydroxyalkyl groups are hydroxymethyl or hydroxyethyl.

Within the formula (IV), the term "dialkylamino" refers to the group —NR$^{24}$R$^{25}$, wherein R$^{24}$ and R$^{25}$ are lower alkyl and the term "lower alkyl" has the previously given significance. A preferred dialkylamino group is dimethylamino. The term "lower alkanoyl" refers to the group —CO—R$^{24}$, wherein R$^{24}$ is lower alkyl and the term "lower alkyl" has the previously given significance. Preferred is a group —CO—R$^{24}$, wherein R$^{24}$ is methyl, meaning an acetyl group. The term "carbamoyl" refers to the group —CO—NH$_2$. The term "lower phenylalkyl" or "phenyl-$C_{1-8}$-alkyl" to lower alkyl groups as defined above wherein at least one of the hydrogen atoms of the lower alkyl group is replaced by a phenyl group. Preferred lower phenylalkyl groups are benzyl or phenethyl.

Within the formula (IV), the term "heteroaryl" refers to an aromatic 5- or 6-membered ring which can comprise one, two or three atoms selected from nitrogen, oxygen and/or sulphur. Examples of heteroaryl groups are e.g. furyl, pyridyl, pyrazinyl, pyrimidinyl, pyridazinyl, thienyl, isoxazolyl, thiazolyl, isothiazolyl, oxazolyl, imidazolyl, or pyrrolyl. Especially preferred are pyridyl, thiazolyl and oxazolyl. The term "lower heteroarylalkyl" or "heteroaryl-$C_{1-8}$-alkyl" refers to lower alkyl groups as defined above wherein at least one of the hydrogen atoms of the lower alkyl group is replaced by a heteroaryl group as defined above. The term "heterocyclyl" refers to a saturated or partly unsaturated 5- or 6-membered ring which can comprise one, two or three atoms selected from nitrogen, oxygen and/or sulphur. Examples of heterocyclyl rings include piperidinyl, piperazinyl, azepinyl, pyrrolidinyl, pyrazolidinyl, imidazolinyl, imidazolidinyl, oxazolidinyl, isoxazolidinyl, morpholinyl, thiazolidinyl, isothiazolidinyl, thiadiazolylidinyl, dihydrofuryl, tetrahydrofuryl, dihydropyranyl, tetrahydropyranyl, and thiomorpholinyl. A preferred heterocyclyl group is piperidinyl. The term "lower heterocyclylalkyl" or "heterocyclyl-$C_{1-8}$-alkyl" refers to lower alkyl groups as defined above wherein at least one of the hydrogen atoms of the lower alkyl group is replaced by a heterocyrlyl group as defined above. The term "form a 4-, 5-, 6- or 7-membered heterocyclic ring optionally containing a further heteroatom selected from nitrogen, oxygen or sulfur" refers to a N-heterocyclic ring, which may optionally contain a further nitrogen, oxygen or sulfur atom, such as azetidinyl, pyrrolidinyl, imidazolidinyl, pyrazolidinyl, oxazolidinyl, isoxazolidinyl, thiazolidinyl, isothiazolidinyl, piperidinyl, piperazinyl, morpholinyl, thiomorpholinyl, or azepanyl. A "4-, 5-, 6- or 7-membered heterocyclic ring containing a sulfinyl group or a sulfonyl group" means a N-heterocyclic ring that contains a —S(O)— group or a —SO$_2$— group, for example 1-oxothiomorpholinyl or 1,1-dioxothiomorpholinyl. The heterocyclic ring may be unsubstituted or substituted by one, two or three groups independently selected from lower alkyl, lower alkoxy and oxo. The heterocyclic ring may also be condensed with a phenyl ring, said phenyl ring being unsubstituted or substituted by one, two or three groups independently selected from lower alkyl, lower alkoxy and halogen. An example for such a condensed heterocyclic ring is 3,4-dihydro-1H-isoquinoline. The term "oxo" means that a C-atom of the heterocyclic ring may be substituted by =O, thus meaning that the heterocyclic ring may contain one or more carbonyl (—CO—) groups. The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared from addition of an inorganic base or an organic base to the free acid. Salts derived from an inorganic base include but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylainine, diethylamine, triethylamine, tripropylalmine, ethanolamine, lysine, arginine, N-ethylpiperidine, piperidine, polymine resins and the like. The compound of formula (IV) can also be present in the form of zwitterions. Particularly preferred pharmaceutically acceptable salts of compounds of formula (IV) are the hydrochloride salts.

The compounds of formula (IV) can also be solvated, e.g. hydrated. The solvation can be effected in the course of the manufacturing process or can take place e.g. as a consequence of hygroscopic properties of an initially anhydrous compound of formula (IV) (hydration). The term pharmaceutically acceptable salts also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

Examples of compounds of formula (IV) are the following: 8-(1-isopropyl-piperidin-4-yloxy)-3,4-dihydro-2H-pyrazino[1,2-a]indol-1-one; 8-(3-piperidin-1-yl-propoxy)-3,4-dihydro-2H-pyrazino[1,2-a]indol-1-one; 8-(1-cyclopropylmethyl-piperidin-4-yloxy)-3,4-dihydro-2H-pyrazino[1,2-a]indol-1-one; 8-[3-((R)-3-hydroxy-pyrrolidin-1-yl)-propoxy] 3,4-dihydro-2H-pyrazino[1,2-a]indol-1-one; 8-[3-((R)-2-methyl-pyrrolidin-1-yl)-propoxy]-3,4-dihydro-2H-pyrazino[1,2-a]indol-1-one; 8-[3((S)-2-methyl-pyrrolidin-1-yl)-propoxy]-3,4-dihydro-2H-pyrazino[1,2-a]indol-1-one; 8-[3-((2S,5S)-2,5-dimethyl-pyrrolidin-1-yl)-propoxy]-3,4-dihydro-2H-pyrazino[1,2-a]indol-1-one; (R)-8-(1-isopropyl-piperidin-4-yloxy)-4-methyl-3,4-dihydro-2H-pyrazino[1,2-a]indol-1-one; (R)-4-methyl-8-(3-piperidin-1-yl-propoxy)-3,4-dihydro-2H-pyrazino[1,2-a]indol-1-one; (R)-8-[3 (R)-3-hydroxy-pyrrolidin-1-yl)-propoxy]-4-methyl-3,4-dihydro-2H-pyrazino[1,2-a]indol-1-one; (S)-8-(1-isopropyl-piperidin-4-yloxy)-4-methyl-3,4-dihydro-2H-pyrazino[1,2-a]indol-1-one; (S)-4-hydroxymethyl-8-(1-isopropyl-piperidin-4-yloxy)-3,4-dihydro-2H-pyrazino[1,2-a]indol-1-one; (S)-8-(1-isopropyl-piperidin-4-yloxy)-3-methyl-3,4-dihydro-2H-pyrazino[1,2-a]indol-1-one; (R)-8-(1-isopropyl-piperidin-4-yloxy)-3-methyl-3,4-dihydro-2H-pyrazino[1,2-a]indol-1-one; 9-(1-isopropyl-piperidin-4-yloxy)-2,3,4,5-tetrahydro[1,4]diazepino[1,2-a]indol-1-one; 9-(3-pyrrolidin-1-yl-propoxy)-2,3,4,5-tetrahydro-[1,4]diazepino[1,2-a]indol-1-one; 2-cyclopropylmethyl-8-(1-isopropyl-piperidin-4-yloxy)-3,4-dihydro-2H-pyrazino[1,2-a] indol-1-one; 8-(1-isopropyl-piperidin-4-yloxy)-2-(2-methoxyethyl)-3,4-dihydro-2H-pyrazino[1,2-a]indol-1-one; 8-(1-isopropyl-piperidin-4-yloxy)-2-(2,2,2-trifluoro-ethyl)-3,4-dihydro-2H-pyrazino[1,2-a]indol-1-one; 8-(1-isopropyl-piperidin-4-yloxy)-2-methyl-3,4-dihydro-2H-pyrazino[1,2-a] indol-1-one; 2-ethyl-8-(1-isopropyl-piperidin-4-yloxy)-3,4-dihydro-2H-pyrazino[1,2-a]indol-1-one; 2-isopropyl-8-(1-isopropyl-piperidin-4-yloxy)-3,4-dihydro-2H-pyrazino[1,2-a]indol-1-one; (R)-2-cyclopropylmethyl-8-(1-isopropyl-piperidin-4-yloxy)-4-methyl-3,4-dihydro-2H-pyrazino[1,2-a]indol-1-one; (R)-8-(1-isopropyl-piperidin-4-yloxy)-2-(2-methoxyethyl)-4-methyl-3,4-dihydro-2H-pyrazino[1,2-a]indol-1-one; (R)-8-(1-isopropyl-piperidin-4-yloxy)-2,4-dimethyl-3,4-dihydro-2H-pyrazazino[1,2a]indol-1-one; (R)-8-(1-isopropyl-piperidin-4-yloxy)-4-methyl-2-(2,2,2-trifluoroethyl]-3,4-dihydro-2H-pyrazino[1,2-a]indol-1-one; 2-ethyl-8-(1-isopropyl-piperidin-4-yloxy)-4-methyl-3,4-dihydro-2H-pyrazino[1,2-a]indol-1-one; (S)-2-cyclopropylmethyl-8-(1-isopropyl-piperidin-4-yloxy)-4-methyl-3,4-dihydro-2H-pyrazino[1,2-a]indol-1-one; (S)-8-(1-isopropyl-piperidin-4-yloxy)-2-(2-methoxy-ethyl)-4-methyl-3,4-dihydro-2H-pyrazino[1,2-a]indol-1-one; (S)-2-cyclopropylmethyl-8-(1-isopropyl-piperid in-4-yloxy)-3-methyl-3,4-dihydro-2H-pyraino[1,2-a]indol-1-one; (S)-8-(1-isopropyl-piperidin-4-yloxy)-2-(2-methoxyethyl)-3-methyl-3,4-dihydro-2H-pyrazino[1,2-a]indol-1-one; (R)-2-cyclopropylmethyl-8-(1-isopropyl-piperidin-4-yloxy)-3-methyl-3,4-dihydro-2H-pyrazino[1,2-a]indol-1-one; (R)-8-(1-isopropyl-piperidin-4-yloxy)-2-(2-methoxyethyl)-3,4-dihydro-2H-pyrazino[1,2-a]indol-1-one; 2-[8-(1-isopropylpiperidin-4-yloxy)-1-oxo-3,4-dihydro-1H-pyrazino[1,2-a]indol-2-yl]-acetamide; 2-[8-(1-isopropyl-piperidin-4-yloxy)-1-oxo-3,4-dihydro-1H-pyrazino[1,2-a]indol-2-yl]-N-methyl-acetamide; 2-[8-(1-isopropyl-piperidin-4-yloxy)-1-oxo-3,4-dihydro-1H pyrazino[1,2-a]indol-2-yl]-N,N-dimethyl-acetamide; 8-(1-isopropyl-piperidin-4-yloxy)-2-(2-morpholin-4-yl-2-oxo-ethyl)-3,4-dihydro-2H-pyrazino[1,2-a] indol-1-one; N-isopropyl-2-[8-(1-isopropyl-piperidin-4-yloxy)-1-oxo-3,4-dihydro-1H-pyrazino[1,2-a]indol-2-yl]-acetamide; N,N-diisopropyl-2-[8-(1-isopropyl-piperidin-4-yloxy)-1-oxo-3,4-dihydro-1H-pyrazino[1,2-a]indol-2-yl]-acetamide; 2-[8-(1-isopropyl-piperidin-4-yloxy)-1-oxo-3,4-dihydro-1H-pyrazino[1,2-a]indol-2-yl]-N-phenyl-acetamide; 2-benzyl-8-(1-isopropyl-piperidin-4-yloxy)-3,4-dihydro-2H-pyrazino[1,2a]indol-1-one; 8-(1-isopropyl-piperidin-4-yloxy)-2-(2-trifluoromethylbenzyl)-3,4-dihydro-2H-pyrazino[1,2-a]indol-1-one; 8-(1-isopropyl-piperidin-4-yloxy)-2-(3-trifluoromethylbenzyl)-3,4-dihydro-2H-pyrazino[1,2-a]indol-1-one; 8-(1-isopropyl-piperidin-4-yloxy)-2-(4-triftuoromethyl-benzyl)-3,4-dihydro-2H-pyrazino[1,2-a]indol-1-one; 8-(1-isopropyl-piperidin-4-yloxy)-2-(2-methoxy-benzyl)-3,4-dihydro-2H-pyrazino[1,2-a]indol-1-one; 8-(1-isopropyl-piperidin-4-yloxy)-2-(3-methoxy-benzyl)-3,4-dihydro-2H-pyrazino[1,2-a]indol-1-one; 8-(1-isopropyl-piperidin-4-yloxy)-2-(4-methoxy-benzyl)-3,4-dihydro-2H-pyrazino[1,2-a]indol-1-one; 2-(2-fluoro-benzyl)-8-(1-isopropyl-piperidin-4-yloxy)-3,4-dihydro-2H-pyrazino[1,2-a]indol-1-one; 2-(3-fluoro-benzyl)-8-(1-isopropyl-piperidin-4-yloxy)-3,4-dihydro-2H-pyrazino[1,2-a]indol-1-one; 2-(4-fluoro-benzyl)-8-(1-isopropyl-piperidin-4-yloxy)-3,4-dihydro-2H-pyrazino[1,2-a]indol-1-one; 2-[8-(1-isopropyl-piperidin-4-yloxy)-1-oxo-3,4-dihydro-1H-pyrazino[1,2-a]indol-2-ylmethyl]-benzonitrile; 3-[8-(1-isopropyl-piperidin-4-yloxy)-1-oxo-3,4-dihydro-1H-pyrazino[1,2-a]indol-2-ylmethyl]-benzonitrile; 4-[8-(1-isopropyl-piperidin-4-yloxy)-1-oxo-3,4-dihydro-1H-pyrazino[1,2-a]indol-2-ylmethyl]-benzonitrile; 8-(1-isopropyl-piperidin-4-yloxy)-2-pyridin-2-ylmethyl-3,4-dihydro-2H-pyrazino[1,2-a]indol 1-one; 8-(1-isopropyl-piperidin-4-yloxy)-2-pyridin-3-ylmethyl-3,4-dihydro-2H- pyrazino[1,2-a]indol-1-one; 8-(1-sopropyl-piperidin-4-yloxy)-2-pyridin-4-methyl-3,4-dihydro-2H-pyrazino[1,2-a]indol-1-one; 8-(1-isopropyl-piperidin-4-yloxy)-2-(1-phenyl- ethyl)-3,4-dihydro-2H-pyrazino[1,2-a] indol-1-one; 2-(3-hydroxy-propyl)-8-(1-isopropyl-piperidin-4-yloxy)-3,4-dihydro-2H-pyrazino[1,2-a]indol 1-one; 2-(2-hydroxy-ethyl)-8-(1-isopropyl-piperidin-4-yloxy)-3,4-dihydro-2H-pyrazino[1,2-a]indol-1-one; (R)-2- benzyl-8-(1-isopropyl-piperidin-4-yloxy)-4-methyl-3,4-dihydro-2H-pyrazino[1,2-a]indol-1-one; (R)-8-(1-isopropyl-piperidin-4-yloxy)-4-methyl-2-pyridin-2-ylmethyl-3,4-dihydro-2H-pyrazino[1,2-a]indol-1-one; (R)-8-(1-isopropyl-piperidin-4-yloxy)-4-methyl-2-pyridin-3-ylmethyl-3,4-dihydro-2H-pyrazino[1,2-a]indol-1-one; (R)-8-(1-isopropyl-piperidin-4-yloxy)-4-methyl-2-pyridin-4-ylmethyl-3,4-dihydro-2H-pyrazino[1,2-a]indol-1-one; (R)-8-(1-isopropyl-piperidin-4-yloxy)-4-methyl-2-(2-methyl-thiazol-4-ylmethyl)-3,4-dihydro-2H-pyrazino[1,2-a]indol-1-one; (R)-8-(1-isopropyl-piperidin-4-yloxy)-4-methyl-2-(5-methyl-2-phenyl-oxazol-4-ylmethyl)-3,4-dihydro-2H-pyrazino[1,2-a]indol-1-one; (R)-8-(1-isopropyl-piperidin-4-yloxy)-4-methyl-2-(5-phenyl-[1,2,4]oxadiazol-3-ylmethyl)-3,4-dihydro-2H-pyrazino[1,2-a]indol-1-one; (R)-2-(3,5-dimethyl-isoxazol-4-ylmethyl)-8-(1-isopropyl-piperidin-4-yloxy)-4-methyl-3,4-dihydro-2H-pyrazino[1,2-a]indol-1-one; (R)-8-(1-isopropyl-piperidin-4-yloxy)-4-methyl-2-(5-methyl-3-phenyl-isoxazol-4-ylmethyl)-3,4-dihydro-2H-pyrazino[1,2-a]indol-1-one; (R)-8-(1-isopropyl-piperidin-4-yloxy)-4-methyl-2-(5-methyl-isoxazol-3-ylmethyl)-3,4-dihydro-2H-pyrazino[1,2-a]indol-1-one; (R)-2-(3-hydroxy-propyl)-8-(1-isopropyl-piperidin-4-yloxy)-4-methyl-3,4-dihydro-2H-pyrazino[1,2-a]indol-1-one; (R)-2-(2-hydroxy-ethyl)-8-(1-isopropyl-piperidin-4-yloxy)-4-methyl-3,4-dihydro-2H-pyrazino[1,2-a]indol-1-one; (R)-8-(1-isopropyl-piperidin-4-yloxy)-4-methyl-2-((R)-4,4,4-trifluoro-3-hydroxy-butyl)-3,4-dihydro-2H-pyrazino[1,2-a]indol-1-one; (R)-2-acetyl-8-(1-isopropyl-piperidin-4-yloxy)-4-methyl-3,4-dihydro-2H-pyrazino[1,2-a]indol-1-one; (R)-2-benzenesulfonyl-8-(1-isopropyl-piperidin-4-yloxy)-4-methyl-3,4-dihydro-2H-pyrazino[1,2-a]indol-1-one; (S)-2-cyclopropylmethyl-4-hydroxymethyl-8-(1-isopropyl-piperidin-4-yloxy)-3,4-dihydro-2H-pyrazino[1,2-a]indol-1-one; (S)-2-cyclopropylmethyl-8-(1-isopropyl-piperidin-4-yloxy)-4-methoxymethyl-3,4-dihydro-2H-pyrazino[1,2-a]indol-1-one; (S)-4-hydroxymethyl-8-(1-isopropyl-piperidin-4-yloxy)-2-methyl-3,4-dihydro-2H-pyrazino[1,2-a]indol-1-one; 2-cyclopropylmethyl-9-isopropyl-piperidin-4-yloxy)-2,3,4,5-tetrahydro-[1,4]diazepino[1,2-a]indol-1-one; 9-(1-isopropyl-piperidin-4-yloxy)-2-(2-methoxy-ethyl)-2,3,4,5-tetrahydro-[1,4]diazepino[1,2-a]indol-1-one; 2-cyclopropylmethyl-9-(3-pyrrolidin-1-yl-propoxy)-2,3,4,5-tetrahydro-[1,4]diazepino[1,2-a]indol-1-one, 2-(2-methoxy-ethyl)-9-(3-pyrrolidin-1-yl-propoxy)-2,3,4,5-tetrahydro-[1,4]diazepino[1,2-a]indol-1-one; (R)-10-chloro-8-(1-isopropyl-piperidin-4-yloxy)-4-methyl-3,4-dihydro-2H-pyrazino[1,2-a]indol-1-one; (R)-10-bromo-8-(1-isopropyl-piperidin-4-yloxy)-4-methyl-3,4-dihydro-2H-pyrazino[1,2-a]indol-1-one; 7-(1-isopropyl-piperidin-4-yloxy)-3,4-dihydro-2H-2,4a,5-triaza-fluoren-1-one; 7-[3((S)-2-methyl-pyrrolidin-1-yl)-propoxy]-3,4-dihydro-2H-2,4a,5-triaza-fluoren-1-one; 7-[3-((R)-2-methyl-pyrrolidin-1-yl)-propoxy]-3,4-dihydro-2H-2,4a,5-triaza-fluoren-1-one; 7-[3-((2R,5R)-2,5-dimethyl-pyrrolidin-1-yl)-propoxy]-3,4-dihydro-2H-2,4a,5-triaza-fluoren-1-one; 7-(1-cyclopropylmethyl-piperidin-4-yloxy)-3,4-dihydro-2H-2,4a,5-triaza-fluoren-1-one; 2-cyclopropylmethyl-7-(1-isopropyl-piperidin-4-yloxy)-3,4-dihydro-2H-2,4a,5-triaza-fluoren-1-one; 7-(1-isopropyl-piperidin-4-yloxy)-2-(2-methoxy-ethyl)-3,4-dihydro-2H-2,4a,5-triaza-fluoren-1-one; 7-(1-isopropyl-pipericlin-4-yloxy)-2-(2,2,2-trifluoroethyl)-3,4-dihydro-2H-2,4a,5-triaza-fluoren-1-one; 7-[3-((S)-2-methyl-pyrrolidin-1-yl)-propoxy]-2-(2,2,2-trifluoroethyl)-3,4-dihydro-2H-2,4a,5-triaza-fluoren-1-one; (R)-7-bromo-8-(1-isopropyl-piperidin-4-yloxy)-4-methyl-3,4-dihydro-2H[1,2-a]indol-1-one; (R)-7-bromo-2-cyclopropylmethyl-8-(1-isopropyl-piperidin-4-yloxy)-4-methyl-3,4-dihydro-2H-pyrazino[1,2-a]indol-1-one, and pharmaceutically acceptable salts thereof.

Further lactams which may be made by the invention include intermediates for compounds of formula (Q) and (QQ):

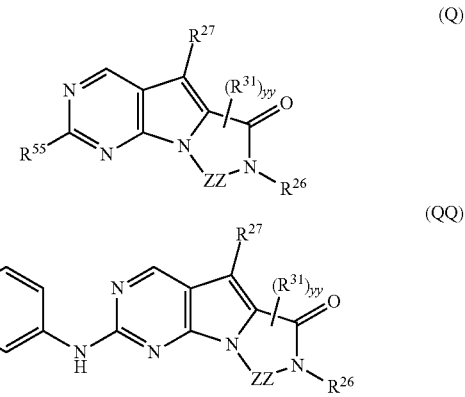

wherein
$R^{26}$ is H, $C_1$-$C_6$ alkyl, or haloalkyl, cycloalkyl, cycloalkyl containing one or more heteroatoms selected from N, O, and S;
each $R^{31}$ is independently aryl, alkyl, cycloalkyl or haloalkyl, wherein each of said alkyl, cycloalkyl and haloalkyl groups optionally includes O or N heteroatoms and two $R^{31}$s on adjacent ring atoms or on the same ring atom together with the ring atom(s) to which they are attached optionally form a 3-8-membered cycle;
yy is 0, 1, 2, 3 or 4;
ZZ is —$(CH_2)_{xx}$— wherein xx is 1, 2, 3 or 4 or —O—$(CH_2)_{xx}$— wherein xx is 2, 3 or 4;
$R^{55}$ is $NHR^4$, $R^4$ is unsubstituted $C_1$-$C_8$ alkyl, cycloalkylalkyl, or -TT-RR, $C_1$-$C_8$ cycloalkyl or cycloalkyl containing one or more heteroatoms selected from N, O, and S, TT is an unsubstituted or substituted $C_1$-$C_6$ alkyl or $C_3$-$C_8$ cycloalkyl linker, and RR is a hydroxyl, unsubstituted or substituted $C_1$-$C_6$ alkoxy, amino, unsubstituted or substituted $C_1$-$C_6$ alkylamino, unsubstituted or substituted di-$C_1$-$C_6$ alkylamino, unsubstituted or substituted $C_6$-$C_{10}$ aryl, unsubstituted or substituted heteroaryl comprising one or two 5- or 6-member rings and 1-4 heteroatoms selected from N, O and S, unsubstituted or substituted $C_3$-$C_{10}$ carbocycle, or unsubstituted or substituted heterocycle comprising one or two 5- or 6-member rings and 1-4 heteroatoms selected from N, O and S;
$R^{77}$ is $(alkylene)_m$-heterocyclo, $(alkylene)_m$-heteroaryl, -$(alkylene)_m$-$NR^3R^4$, -$(alkylene)_m$-$C(O)NR^3R^4$, $(alkylene)_m$-$OR^5$, $(alkylene)_m$-$S(O)_n$—$R^5$, or -$(alkylene)_m$-$S(O)_n$—$NR^3R^4$ any of which may be optionally independently substituted with one or more $R^x$ groups as allowed by valance, and wherein two $R^x$ groups bound to the same or adjacent atoms may optionally combine to form a ring and wherein $R^3$, $R^4$ and $R^5$, m, n, and $R^x$, in these definitions for $R^{77}$ are as defined for formulae (I), (II), or (II).
$R^{27}$ is -$(alkylene)_m$ $C_3$-$C_8$ cycloalkyl, -$(alkylene)_m$ aryl, (alkylene)$_m$-heterocyclo, -$(alkylene)_m$-heteroaryl, (alkylene)$_m$-$NR^3R^4$, -$(alkylene)_m$-$C(O)$—$NR^3R^4$, -$(alkylene)_m$-$O$—$R^5$, -$(alkylene)_m$-$S(O)_n$—$R^5$, or -$(alkylene)_m$-$S(O)_n$—$NR^3R^4$ any of which may be optionally independently substituted with one or more $R^x$ groups as allowed by valance, and wherein two R$^x$ groups bound to the same or adjacent atom(s) may optionally combine to form a ring and wherein R$^3$, R$^4$ and R$^5$, m, n, and R$^x$, in these definitions for R$^{27}$ are as defined for formula (I), (II), or (II). For (Q), R$^{27}$ may also be H, C$_1$-C$_3$ alkyl or haloalkyl. Such compounds of formulae (Q) and (QQ) may be in the form of pharmaceutically acceptable salts.

In some specific cases, an aryl or heteroaryl can be ortho-phenyl substituted by alkyl, cycloalkyl, halo, haloalkyl, thioalkyl, sulfonylalkyl, alkoxy, haloalkoxy, cyano, alkylcarboxamides or aminodialkyl. Aryl and heteroaryl could also be ortho-disubstituted phenyl with alkyl, cycloalkyl, halo, haloalkyl, thioalkyl, sulfonylalkyl, alkoxy, haloalkoxy, cyano, alkylcarboxamides, or aminodialkyl as allowed by valence. Aryl and heteroaryl could also be meta or para substituted with alkyl, cycloalkyl, haloalky, halo, haloalkyl, thioalkyl, sulfonylalkyl, alkoxy, haloalkoxy, cyano, alkylcarboxamides or aminoalkyl.

Chloro Tricyclic Amide (MM) is an example of an intermediate for a compound of formula (Q) or (QQ), which can be made by the process of the present invention.

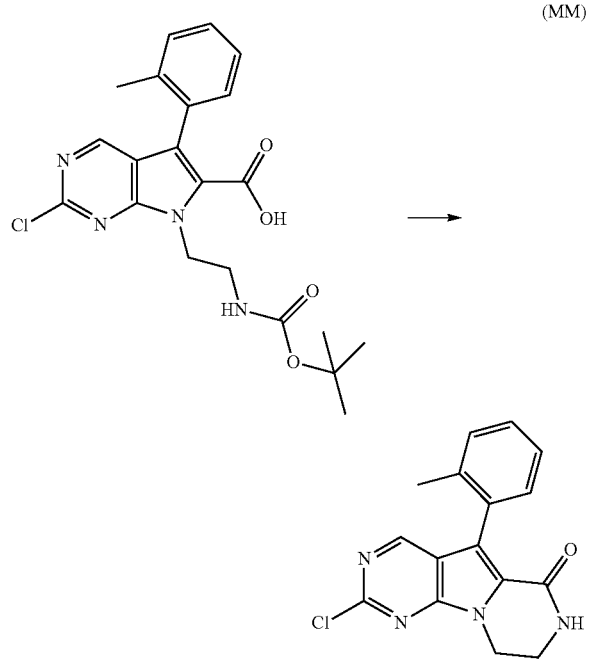 [SMILES: Cc1ccccc1-c1c(C(=O)O)n(CCNC(=O)OC(C)(C)C)c2nc(Cl)ncc12 ; Cc1ccccc1-c1c2n(c3nc(Cl)ncc13)CCNC2=O]

(MM)

To 0.1 g (0.261 mmole) of 7-[2-(tert-butoxycarbonylamino)ethyl]-2-chloro-5-(o-tolyl)pyrrolo[2,3-d]pyrimidine-6-carboxylic acid in DCM (4.1 mL) was added DMAP (20 mg) followed by the addition of N,N-Diisopropylcarbodiimide (0.081 mL 2 eq). After stirring for 3 hrs, trifluoroacetic acid (0.723 mL) was added. Stirring was then continued for another 30 minutes. The reaction mixture was neutralized with satd. NaHCO$_3$. DCM (20 mL) was then added and the organic layer separated, dried with magnesium sulfate and then concentrated under vacuum to afford the crude product which was columned using hexane/ethylacetate (0-100%) to afford chloro tricyclic amide (MM) (0.65 g). LCMS (ESI) 313 (M+H).

In more detail, an important part of this invention is a process to create a lactam. For example, the lactam (QQQ) below may be synthesized from the acid (RRR) according to the invention which comprises cyclizing an acid of the formula (RRR), wherein LG is a leaving group such as the atoms to form alkyl or aryl carbamates such as tBoc. The reaction conditions for the cyclization can be a one step process wherein, the addition of reagents are all done in one pot resulting in the direct formation of the lactam with the loss of LG. In certain cases, an additional step might be desirable for the loss of the LG after lactam formation.

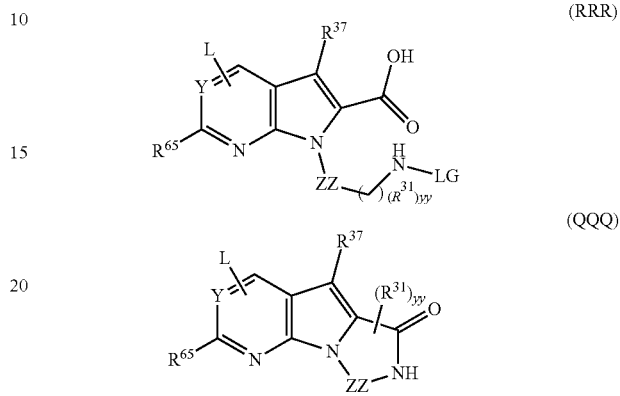

(RRR)

(QQQ)

wherein
R$^{37}$ is a value of R$^8$ for formula (I), (II) or (III) or R$^{37}$ is a value of R$^{14}$ for formula (IV);
R$^{31}$, yy and ZZ are as defined above for (Q);
Y is —CH— or —N;
L as allowed by valance is hydrogen, aryl, heteroaryl, C$_1$-C$_8$ alkoxy, aryloxy, heteroaryloxy, C$_1$-C$_8$ alkyl, cycloalkylalkyl, or -TT-RR as defined above for the formula (Q), C$_1$-C$_8$ cycloalkyl or cycloalkyl containing one or more heteroatoms selected from N, O and S;
R$^{65}$ is any leaving group that can be displaced by primary amine (for example to create an intermediate for a final product), examples of leaving groups being Cl, Br, I, F, SMe, Saryl, Sheteroaryl, SOMe, SO$_2$Me, SOalkyl, SO$_2$alkyl, SOcycloalkyl, SO$_2$cycloalkyl, SOaryl, SO$_2$aryl, hydroxy, hydroxyalkyl, hydroxyaryl or hydroxyheteroaryl, or R$^{65}$ may be a value of R$^{55}$ for the formula Q above or a value of the aromatic amine portion of each of the left-hand portions depicted in formula (I), (II) and (III), ie. of the subformulae (S), (SS) or (SSS):

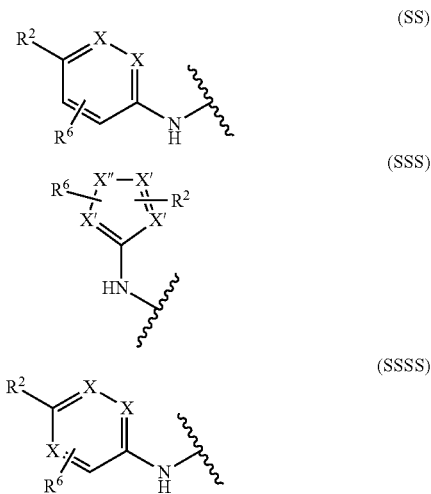

(SS)

(SSS)

(SSSS)

Example: Tricyclic Amide 1

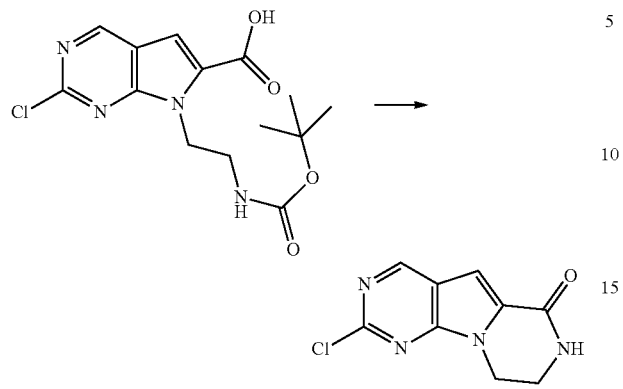

Method A: To 7-[2-(tert-bytoxycarbonylamino)ethyl]2-chloro-pyrrolo[2,3-d]pyrimidine-6-carboxylic acid 0.1 g (0.00029 mole) in DCM (4.5 inL) cooled to 0 degrees is added DMAP (10 mg) and 1-Ethyl-3-(3-dimethylaminopropyl)carbodiimide (0.111 g. 2 eq). After stirring for 30 minutes, TFA (0.8 mL) was added dropwise and the contents stirred for 2 hrs. After neutralization with sat NaHCO3, DCM (50 ml) was added and the organic layer separated, dried (magnesium sulfate) and then concentrated under vacuum to afford the crude product. Column chromatography with hecane/ethyl acetate (O—100%) over silica gel afforded the tricyclic amide 1. $^1$HNMR (d6-DMSO) 9.09 (s, 1H), 8.48 (s,1H). 6.81 (brs. 1H), 7.21 (s. 1H), 4.33 (m. 2H), 3.64 (m. 2H), LCMS (ESI) 223 (M+H).

Method B: To 7-[2-(tert-butoxycarbonylamino)ethyl]-2-chloro-pyrrolo[2,3-d]pyrimidine-6-carboxylic acid 0.1 g (0.00029 mole) in DCM (4.5 mL) cooled to 0 degrees is added DMAP (10 mg) and O-Benzotriazole-N,N,N',N'-tetramethyl-uronium-hexafluoro-phosphate (0.220, 2 eq). After stirring for 30 minutes, trifluoroacetic acid (0.8 mL) is added dropwise and the contents stirred for 2 hrs. After neutralization with sat NaHCO3, DCM (50 mL) is added and the organic layer separated, dried (magnesium sulfate) and then concentrated under vacuum to afford the crude product. Column chromatography with hexane/ethyl acetate (0-100%) over silica gel affords the tricyclic amide 1. The NMR and LCMS data were consistent with the product obtained using Method A.

Method C: To 7-[2-(tert-butoxycarbonylamino)ethyl]-2-chloro-pyrrolo[2,3-d]pyrimidine-6-carboxylic acid 0.1 g (0.00029 mole) in DCM (4.5 mL) cooled to 0 degrees is added DMAP (10 mg) and N,N'-Dicyclohexylcarbodiimide (0.119 g, 2 eq). After stirring for 2 hours, trifluoroacetic acid (0.85 mL) is added dropwise and the contents stirred for 30 minutes. Alter neutralization with sat NaHCO$_3$, DCM (50 mL) is added and the organic layer was separated, dried (magnesium sulfate) and then concentrated under vacuum to afford the crude product. Column chromatography with hexane/ethyl acetate (0-100%) over silica gel affords the tricyclic amide 1. The NMR and LCMS data were consistent with the product obtained using Method A.

Method D: To 7-[2-(tert-butoxycarbonylamino)ethyl]-2-chloro-pyrrolo[2,3-d]pyrimidine-6-carboxylic acid 0.1 g (0.00029 mole) in DCM (4.5 mL) cooled to 0 degrees is added DMAP (10 mg) and trifluoroacetic anhydride (68 uL, 1.7 eq). The contents are warmed to RT and stirred for 2 hrs. After 2 hours, trifluoroacetic acid (0.8 mL) is added and stirring continued for 2 additional hours. After neutralization with sat NaHCO$_3$, DCM (50 mL) is added and the organic layer was separated, dried (magnesium sulfate) and then concentrated under vacuum to afford the crude product. Column chromatography with hexane/ethyl acetate (0-100%) over silica gel affords the tricyclic amide 1. The NMR and LCMS data were consistent with the product obtained using Method A.

What is claimed is:
1. A compound of the formulae (QQQ):

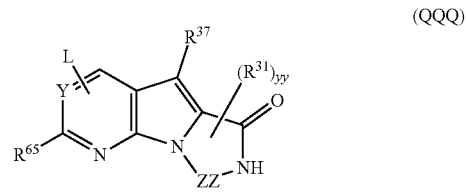

(QQQ)

wherein
$R^{37}$ is H, $C_1$-$C_3$ alkyl, halogen, or haloalkyl;
$R^{31}$ is aryl, alkyl, cycloalkyl, or haloalkyl, wherein each of said alkyl, cycloalkyl, and haloalkyl groups optionally includes O or N heteroatoms and two $R^{31}$s on adjacent ring atoms or on the same ring atom together with the ring atom(s) to which they are attached optionally form a 3-8-membered cycle;
yy is 0, 1, 2, 3, or 4;
ZZ is $(CH_2)_{xx}$— wherein xx is 1, 2, 3, or 4, or —O—$(CH_2)_{xx}$— wherein xx is 2, 3, or 4;
Y is —N—;
L, as allowed by valance, is hydrogen, aryl, heteroaryl, $C_1$-$C_8$ alkoxy, aryloxy, heteroaryloxy, $C_1$-$C_8$ alkyl, cycloalkylalkyl, -TT-RR, $C_3$-$C_8$ cycloalkyl, or cycloalkyl containing one or more heteroatoms selected from N, O, and S;
TT is an $C_1$-$C_6$ alkyl or $C_3$-$C_8$ cycloalkyl linker;
RR is a hydroxyl, $C_1$-$C_6$ alkoxy, amino, $C_1$-$C_6$ alkylamino, di-$C_1$-$C_6$ alkylamino, $C_6$-$C_{10}$ aryl, heteroaryl comprising one or two 5- or 6-member rings and 1-4 heteroatoms selected from N, O, and S, $C_3$-$C_{10}$ carbocycle, or heterocycle comprising one or two 5- or 6-member rings and 1-4 heteroatoms selected from N, O and S; and
$R^{65}$ is Br, I, F, SMe, Saryl, Sheteroaryl, SOMe, SO$_2$Me, SOalkyl, SO$_2$alkyl, SOcycloalkyl, SO$_2$cycloalkyl, SOaryl, SO$_2$aryl, hydroxy, hydroxyalkyl, hydroxyaryl, or hydroxyheteroaryl.

2. The compound of claim 1, wherein $R^{65}$ is SMe, SOMe, SO$_2$Me, SOalkyl, SO$_2$alkyl, SOaryl, or SO$_2$aryl.
3. The compound of claim 1, wherein L is hydrogen.
4. The compound of claim 1, wherein xx is 2.
5. The compound of claim 1, wherein $R^{37}$ is hydrogen.
6. The compound of claim 1, wherein $R^{65}$ is SMe or SOMe.
7. The compound of claim 1, wherein $R^{65}$ is SOalkyl or SOaryl.

8. The compound of claim 1, wherein $R^{65}$ is $SO_2$alkyl.

9. The compound of claim 1, wherein $R^{65}$ is $SO_2Me$.

10. The compound of claim 9, wherein L is hydrogen.

11. The compound of claim 10, wherein xx is 2.

12. The compound of claim 11, wherein $R^{37}$ is hydrogen.

13. The compound of claim 1, wherein the compound is

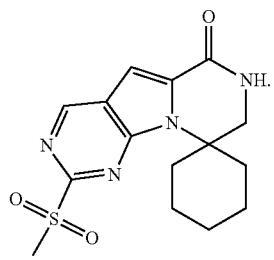 [SMILES: CS(=O)(=O)c1ncc2cc3n(c2n1)C1(CCCCC1)CNC3=O]

14. The compound of claim 1, wherein the compound is

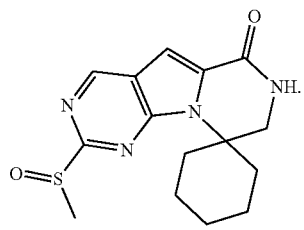 [SMILES: CS(=O)c1ncc2cc3n(c2n1)C1(CCCCC1)CNC3=O]

15. The compound of claim 1, wherein the compound is

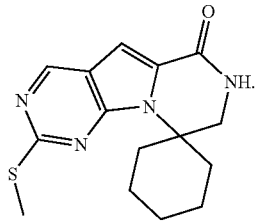 [SMILES: CSc1ncc2cc3n(c2n1)C1(CCCCC1)CNC3=O]

16. The compound of claim 1, wherein the compound is

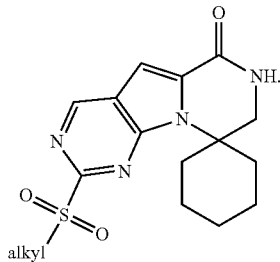

17. The compound of claim 1, wherein the compound is

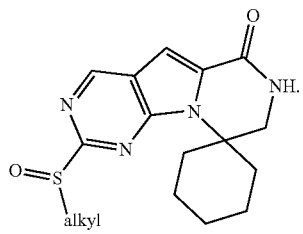

* * * * *